(12) United States Patent
Azar et al.

(10) Patent No.: US 11,813,452 B2
(45) Date of Patent: Nov. 14, 2023

(54) THERAPEUTIC DEVICES FOR PLACEMENT UNDERNEATH THE EYELID AND ASSOCIATED SYSTEMS, DEVICES, AND METHODS FOR DRY EYE TREATMENT

(71) Applicant: Twenty Twenty Therapeutics LLC, South San Francisco, CA (US)

(72) Inventors: Dimitri Azar, San Francisco, CA (US); Fred Shungneng Lee, Sunnyvale, CA (US); Timothy Stowe, Alameda, CA (US)

(73) Assignee: TWENTY TWENTY THERAPEUTICS LLC, South San Francisco, CA (US)

( * ) Notice: Subject to any disclaimer, the term of this patent is extended or adjusted under 35 U.S.C. 154(b) by 0 days.

(21) Appl. No.: 17/940,433

(22) Filed: Sep. 8, 2022

(65) Prior Publication Data
US 2023/0001207 A1    Jan. 5, 2023

Related U.S. Application Data

(63) Continuation of application No. 15/931,241, filed on May 13, 2020, now Pat. No. 11,446,495.
(Continued)

(51) Int. Cl.
*A61N 1/36* (2006.01)
*A61N 1/04* (2006.01)
(Continued)

(52) U.S. Cl.
CPC ....... *A61N 1/36046* (2013.01); *A61N 1/0408* (2013.01); *A61N 1/0476* (2013.01);
(Continued)

(58) Field of Classification Search
CPC ............. A61N 1/36046; A61N 1/0476; A61N 1/36034; A61N 1/36031; A61N 1/3787; A61N 1/3606; A61N 1/3756; A61N 1/36146; A61N 1/37205; A61N 1/0526; A61N 1/0546; A61N 1/36057;
(Continued)

(56) References Cited

U.S. PATENT DOCUMENTS

| | | | |
|---|---|---|---|
| 2016/0114172 A1* | 4/2016 | Loudin | A61N 1/3756 607/53 |
| 2020/0206023 A1* | 7/2020 | Pathak | A61F 7/00 |

* cited by examiner

*Primary Examiner* — Carl H Layno
*Assistant Examiner* — Anh-Khoa N Dinh
(74) *Attorney, Agent, or Firm* — HAYNES AND BOONE LLP

(57) ABSTRACT

A device is presented herein that is configured to be located underneath an eyelid and worn by a user for treating dry eye. The device includes a first surface configured to face a portion of a sclera of the eye, and a second surface configured to face an eyelid and to be completely covered by the eyelid. In some embodiments, the device further includes a plurality of stimulation electrodes proximal to the first surface, wherein the plurality of stimulation electrodes is configured to stimulate the sclera. The device further includes an energy storage element coupled to the plurality of stimulation electrodes. The energy storage element is configured to supply power to the plurality of stimulation electrodes. The device further includes a processor configured to control a supply of energy from the energy storage element to the plurality of stimulation electrodes to stimulate the sclera.

20 Claims, 30 Drawing Sheets

Related U.S. Application Data

(60) Provisional application No. 62/847,593, filed on May 14, 2019.

(51) Int. Cl.
*A61N 1/378* (2006.01)
*A61B 5/053* (2021.01)
*A61B 3/10* (2006.01)

(52) U.S. Cl.
CPC ..... *A61N 1/36031* (2017.08); *A61N 1/36034* (2017.08); *A61N 1/3787* (2013.01); *A61B 3/101* (2013.01); *A61B 5/053* (2013.01)

(58) Field of Classification Search
CPC ............ A61N 1/37211; A61N 1/37247; A61N 1/3758; A61N 1/0456; A61N 1/0472; A61N 1/0484; A61N 1/36014; A61N 1/36025; A61N 1/3603; A61N 1/0543; A61N 1/08; A61N 1/306; A61N 1/327; A61N 1/0404; A61N 1/0408; A61N 1/0492; A61N 1/0551; A61N 2005/0644; A61N 2005/0659; A61N 5/022; A61N 5/067; A61N 7/00; A61B 5/053; A61B 3/101; A61B 5/0537; A61B 5/1103; A61B 5/6821; A61K 9/0048; A61F 9/00; A61F 9/0017; A61F 2007/0004; A61F 2007/0095; A61F 2009/00861; A61F 2250/0059; A61F 7/00; A61F 9/00745; A61F 9/00772; A61F 9/0079; A61F 9/04
See application file for complete search history.

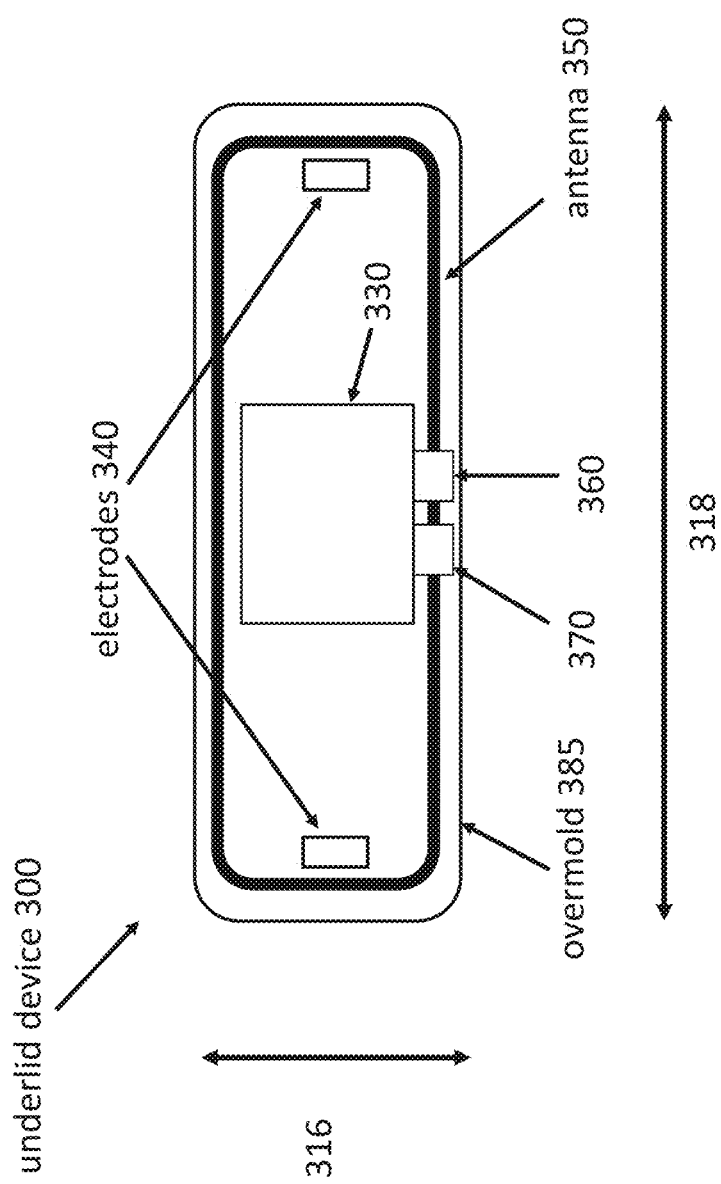

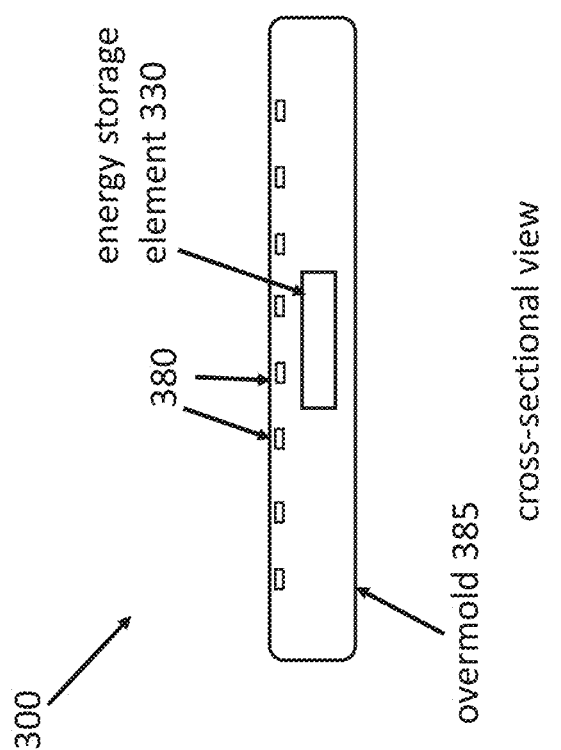

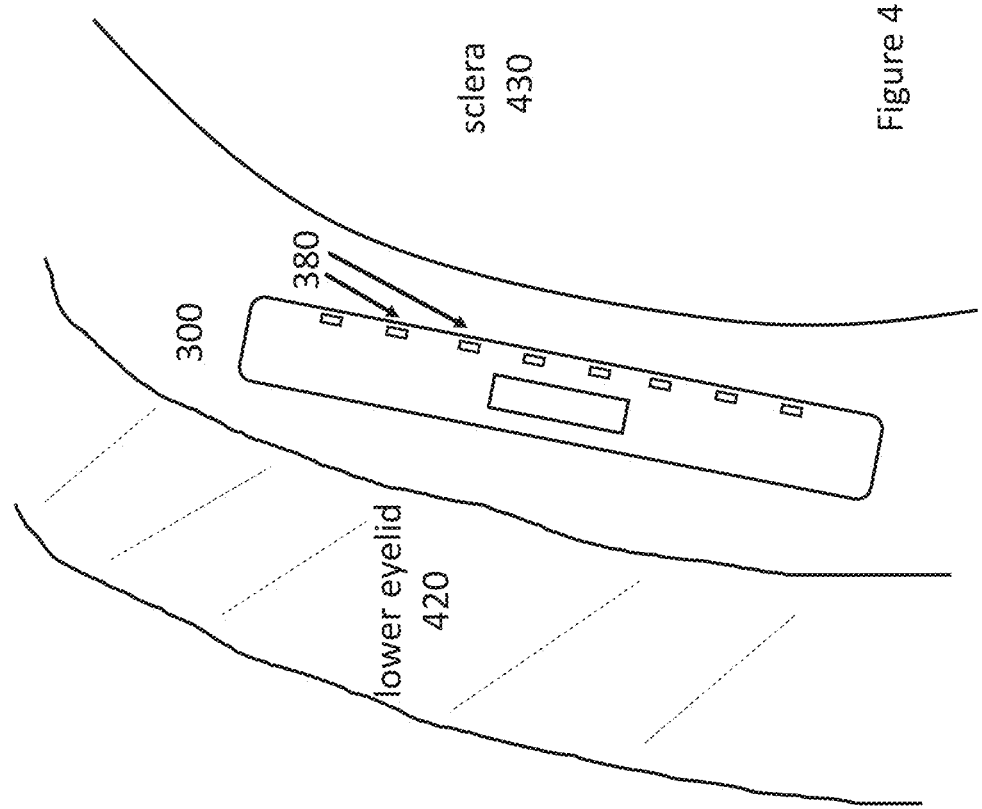

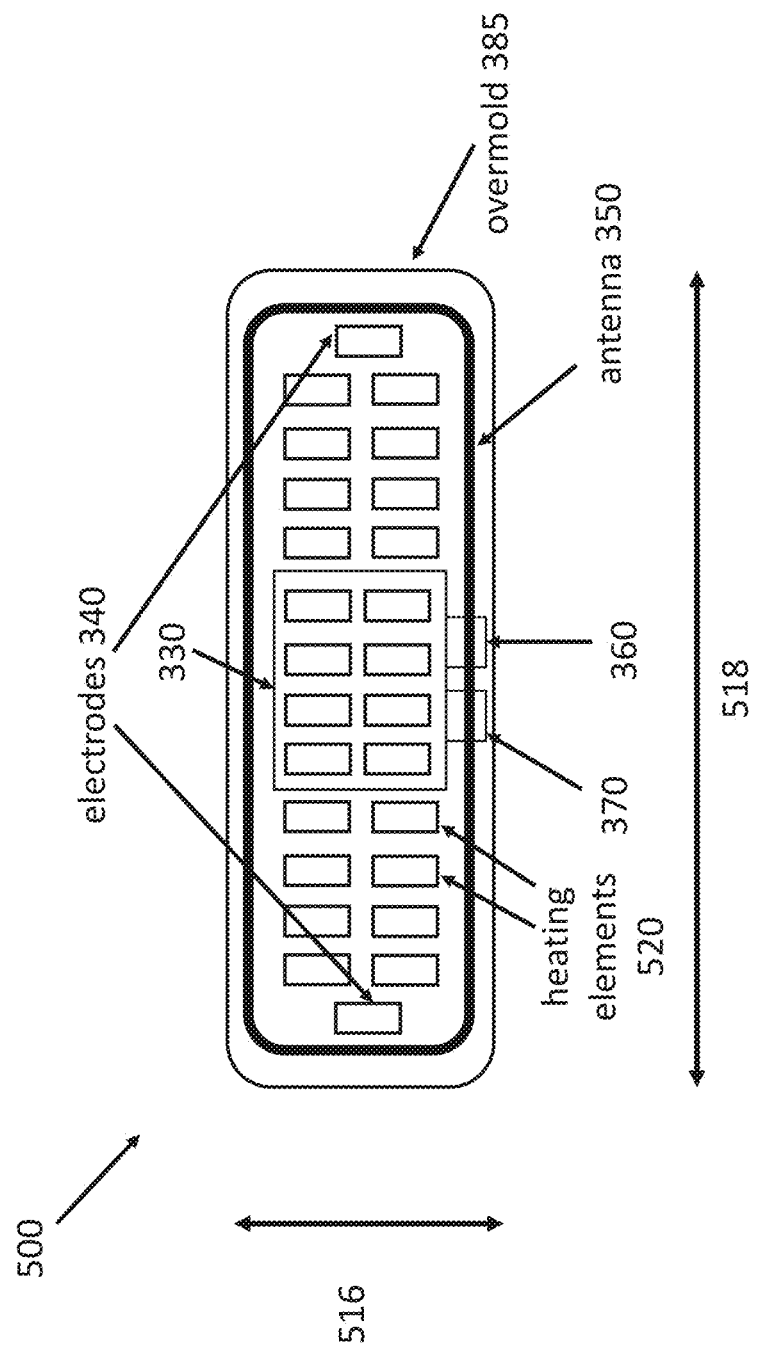

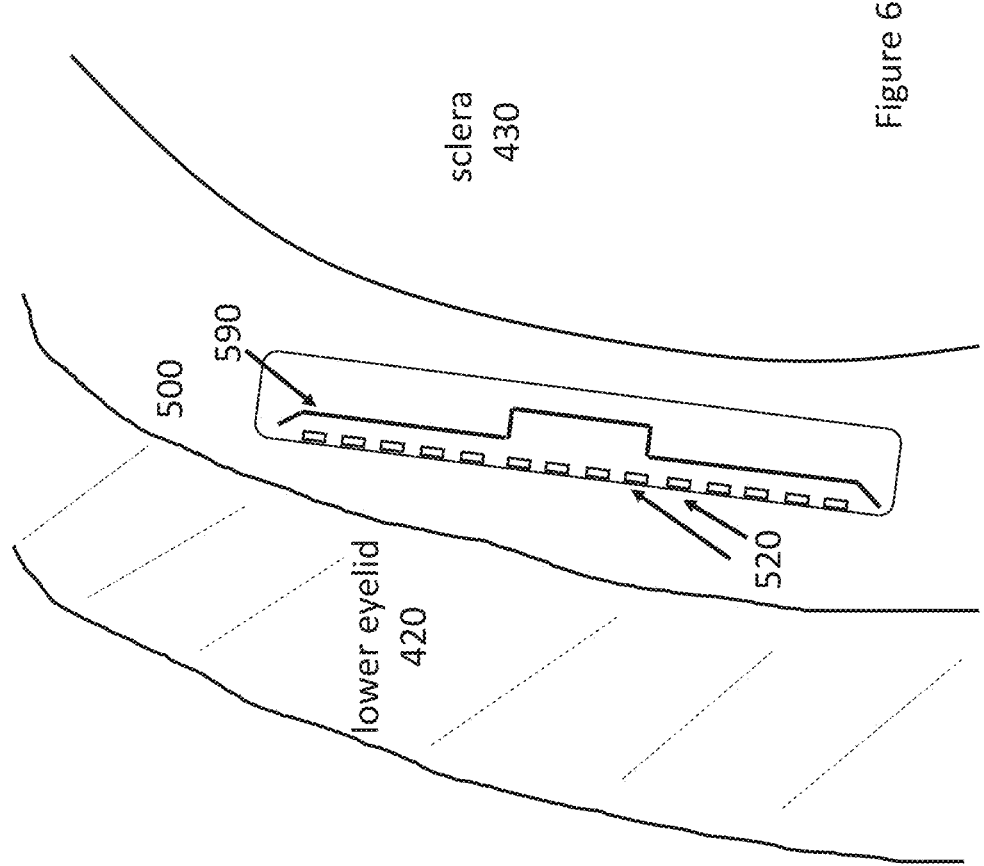

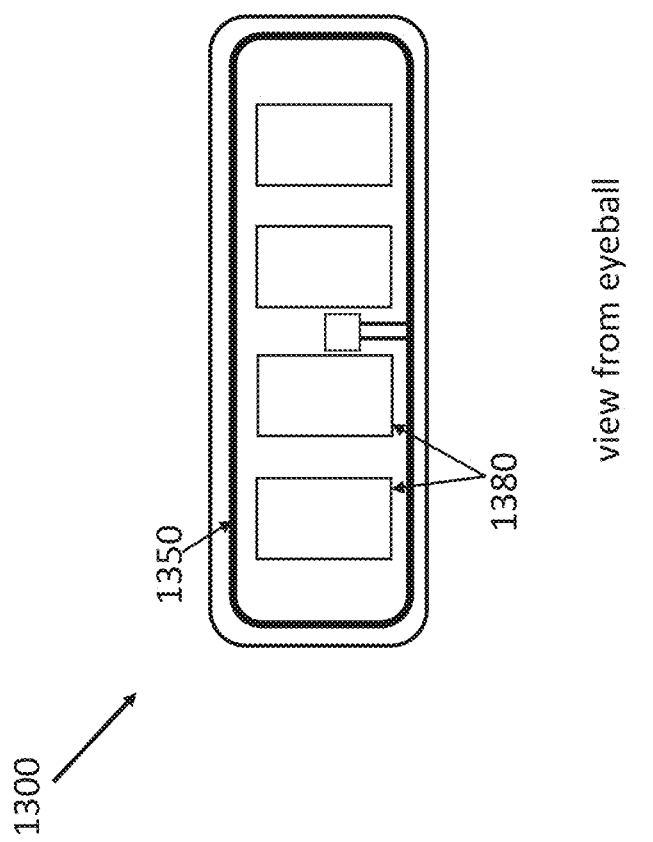

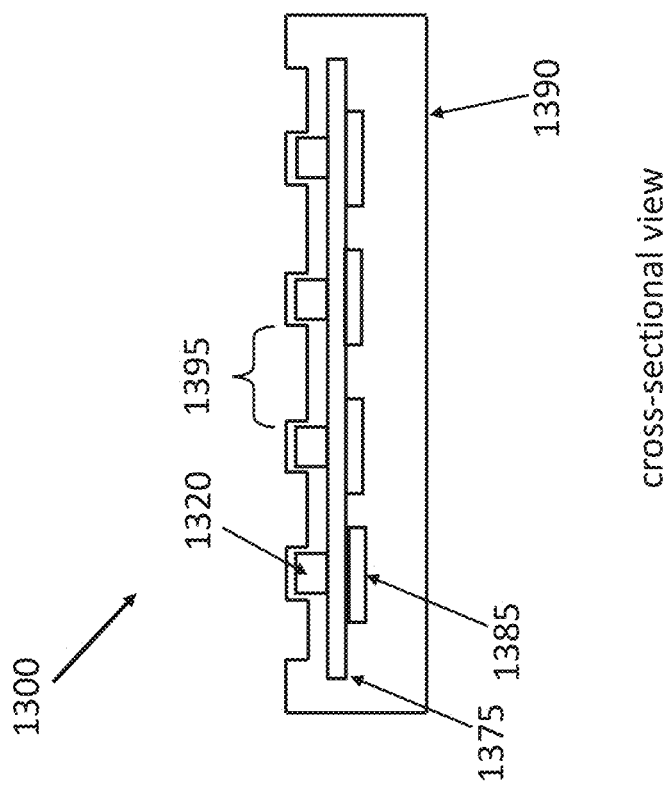

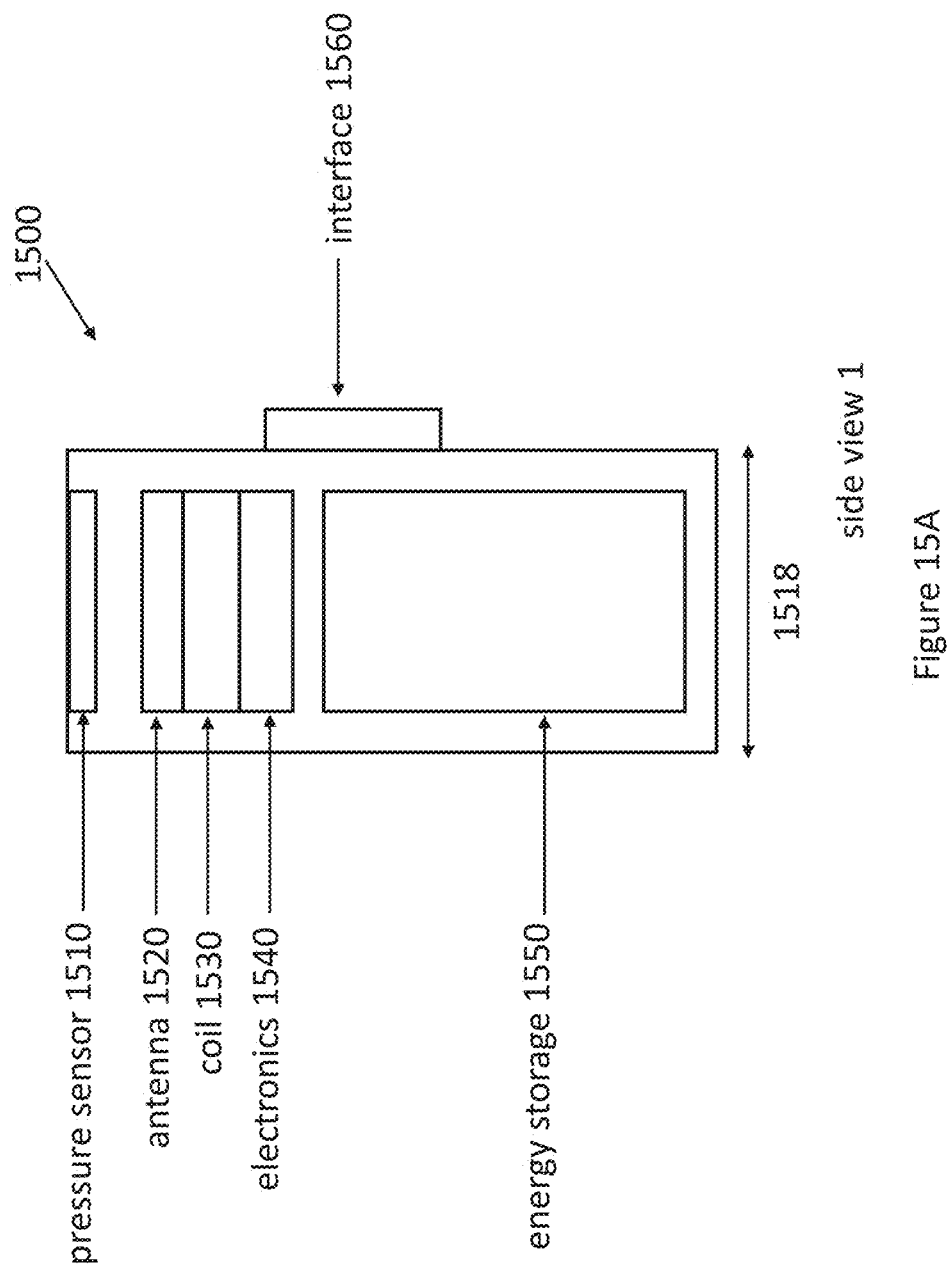

top view

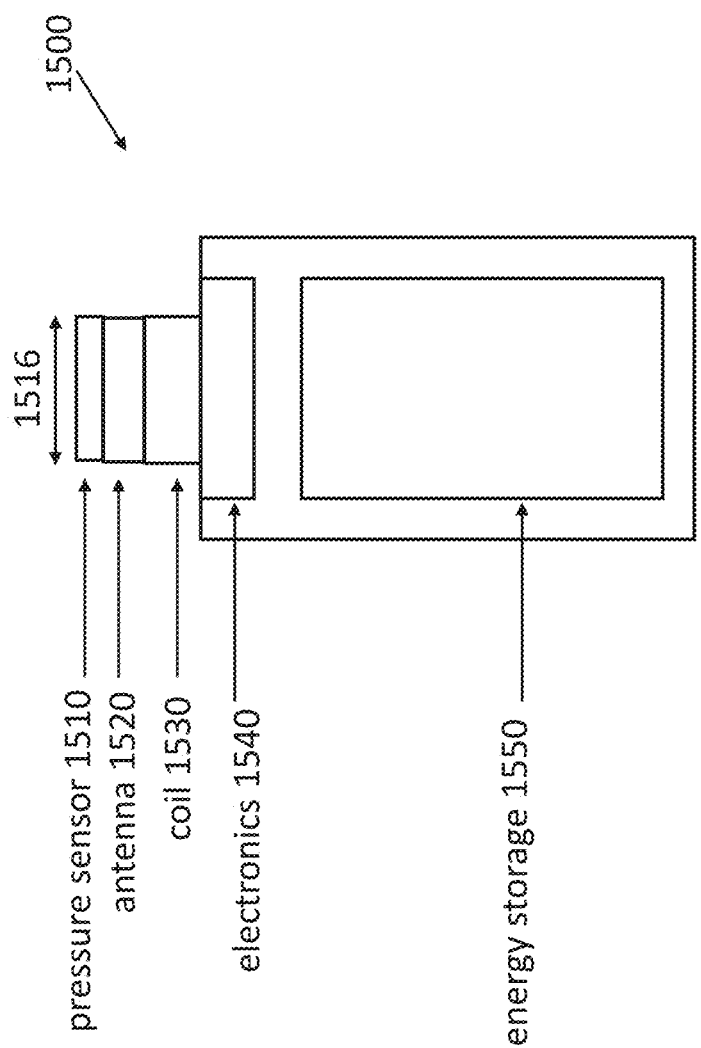

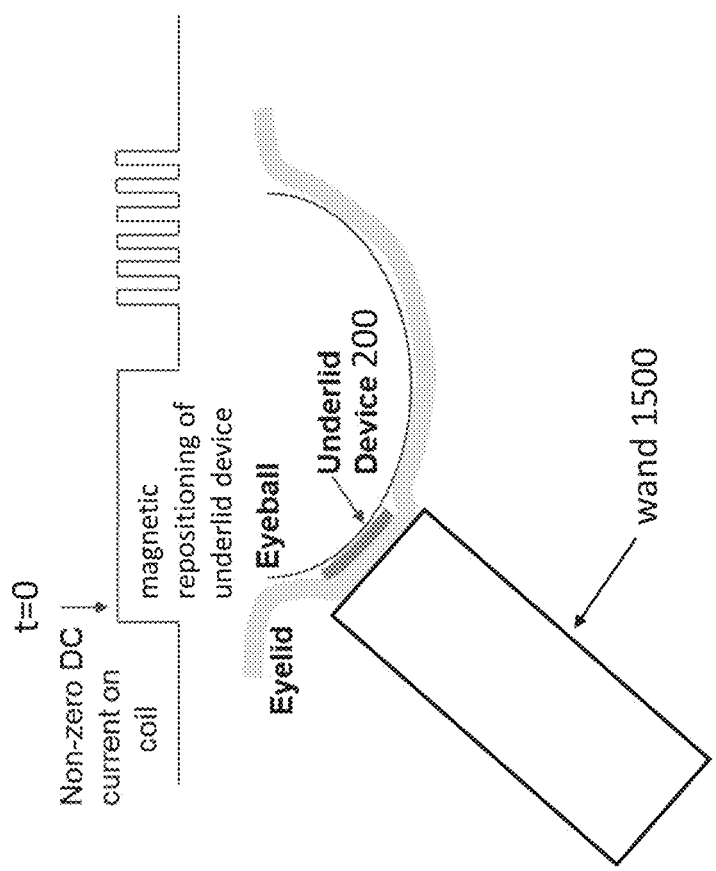

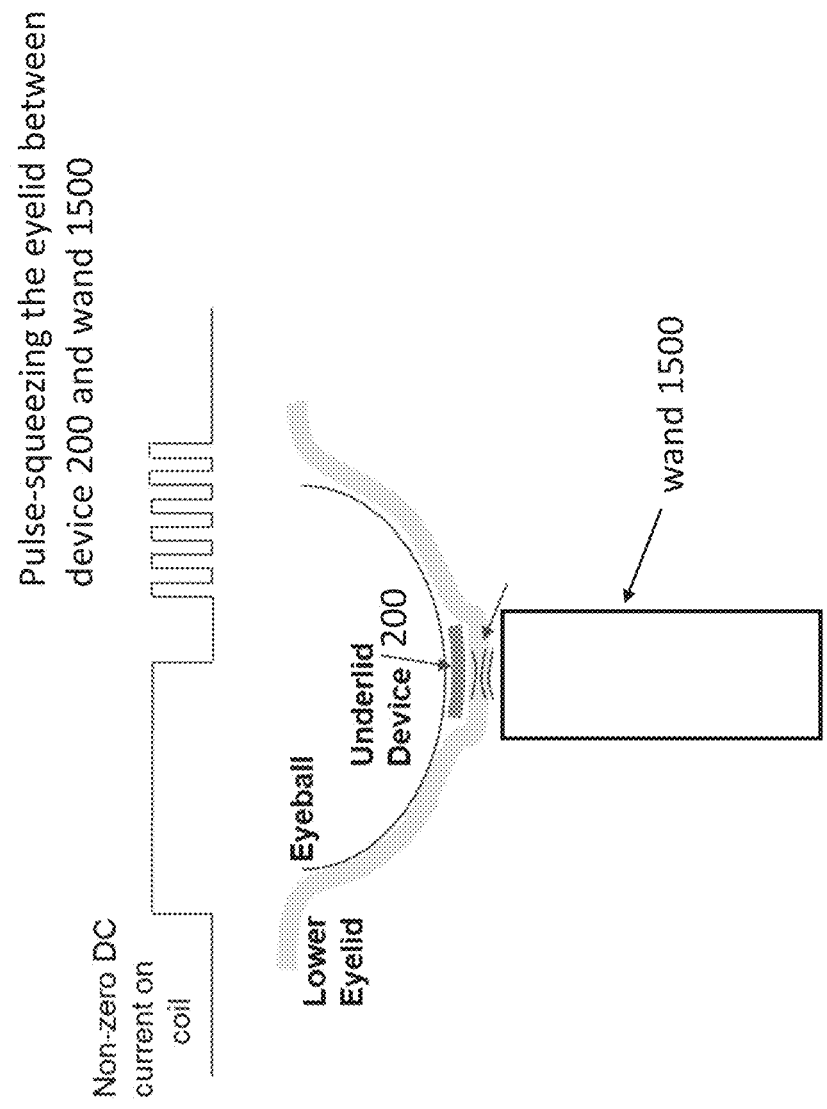

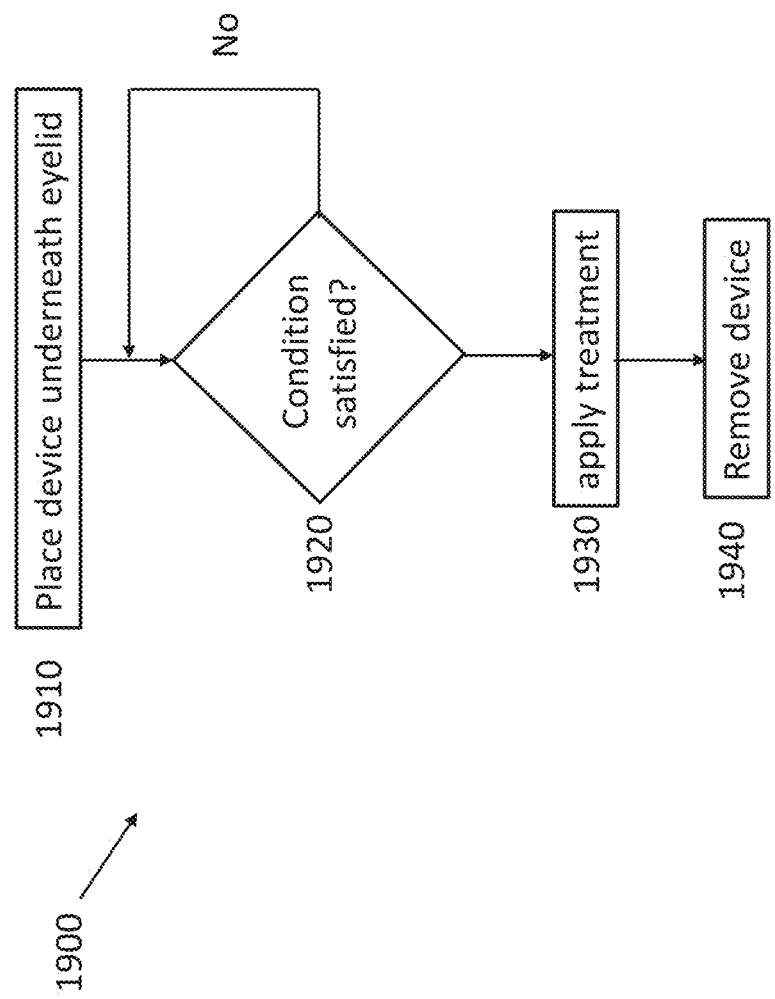

THERAPEUTIC DEVICES FOR PLACEMENT UNDERNEATH THE EYELID AND ASSOCIATED SYSTEMS, DEVICES, AND METHODS FOR DRY EYE TREATMENT

CROSS-REFERENCE TO RELATED APPLICATION(S)

This application claims the benefit of the filing date of, and priority to, U.S. Application No. 62/847,593, filed May 14, 2019, and U.S. application Ser. No. 15/931,241, filed May 13, 2020, now U.S. Pat. No. 11,446,495 B2, and the entire disclosure of each application is hereby incorporated herein by reference.

TECHNICAL FIELD

The present disclosure relates generally to ophthalmic systems and devices and associated methods for treating dry eye, and, in particular but not exclusively, relates to systems and devices and associated methods for placement underneath an eyelid, and out of the field of vision, for stimulating the sclera surface and/or eyelid to trigger blink reflexes or reflex tear production to treat dry eye and/or for heating or otherwise messaging or stimulating Meibomian glands to stimulate meibum production.

BACKGROUND

Dry eye disease affects millions of people worldwide. According to some studies, the third most common reason for visiting an ophthalmologist's office is for dry eye disease symptoms. Recently it has been shown that up to 80% of dry eye cases also have a component called meibomian gland dysfunction or MGD. MGD is related to the absence of, or the severely reduced production of, tear film lipids.

Normally, the lipid layer produced by the meibomian (also expressed as Meibomian) glands spreads evenly into a thin (thickness in nanometers) protective film over the air-tear interface above the cornea. Every time a person blinks a slight amount of lipid protective film may be spread. However, there are many conditions under which this oily layer no longer spreads out evenly over the tear film and this process can be interrupted, reduced, or even stopped entirely. These root causes can include, but are not limited to, hormonal changes in the oil production properties with age, skin mites living in the eyelashes, prolonged infection such as difficult to remove sties, general inflammation (Blepharitis), autoimmune diseases or allergic reactions, and more recently the inadequate blinking from excessive screen time known as computer vision syndrome. The absence of an outer protective lipid layer reduces the evaporation time for the tear film covering the eye leading to interrelated issues of inadequate production of tears and meibum.

In the past mild MGD has been addressed by using warm compresses, eyelid cleansing compounds, and massaging the eyelids gently. However, these approaches have not been shown to clinically be effective in many severe dry eye cases.

Recently, a better in-office ophthalmological treatment, known as LipiFlow®, has shown clinical promise. This treatment works by heating up the meibomian glands in the eyelids and melting the oils which have become clogged. As the eyelids are heated from the inside, heat is delivered directly to the meibomian gland. In addition, air bladders are used to simultaneously provide pulsating mechanical pressure which helps mechanically loosen clogged glands. However, LipiFlow® and other office procedures are still a highly invasive and costly procedure requiring an expert ophthalmologist. Furthermore, treatment may need to be repeated multiple times a year, and the eyes may need local anesthetic applied.

Other known eye treatments include heating the outside of the eyelids using heating pads. In this type of procedure, ophthalmologists still typically use forceps with an intermediate pressure to effectively exercise the glands. In addition, since an office visit is typically required to visit a health care professional, such treatments remain costly.

Some treatments for aqueous deficient dry eye (ADDE) syndrome include application of various types of artificial tears or pharmaceutical-based treatments. Recently, an effective intranasal electroceutical stimulator for dry eye treatment, called TrueTear, was brought to the market.

SUMMARY

The present disclosure advantageously describes devices, systems, and methods for treating dry eye. The present disclosure presents novel electroceutical treatments and devices to the existing portfolio of dry eye therapies. New treatment devices and systems described herein provide a socially-acceptable user experience, hands-free/scheduled treatment options, and sensor/actuator capabilities to further optimize and improve dry eye disease management.

According to some aspects, a device is presented that is configured to be located underneath an eyelid and worn by a user for treating dry eye. The device includes a first surface configured to face a portion of a sclera of the eye, and a second surface configured to face an eyelid and to be completely covered by the eyelid. In some embodiments, the device further includes a plurality of stimulation electrodes proximal to the first surface, wherein the plurality of stimulation electrodes is configured to stimulate the sclera. The device further includes an energy storage element coupled to the plurality of stimulation electrodes, and a processor configured to control a supply of energy from the energy storage element to the plurality of stimulation electrodes to stimulate the sclera.

In some aspects, the present disclosure describes a system for treating dry eye. The system includes an underlid device configured to be positioned between a surface of an eyelid and a surface of an eye. The underlid device includes a first surface configured to face the surface of an eye and a second surface configured to face the eyelid. The underlid device further includes a plurality of stimulation electrodes closer to the first surface than the second surface, wherein the plurality of stimulation electrodes is configured to stimulate the surface of the eye. The system further includes an external device configured to supply power to the underlid device.

In some aspects, the present disclosure describes a method of operating an underlid device for treating an ophthalmic condition. In the method, the underlid device includes a plurality of stimulation electrodes configured to stimulate an eye. The method includes placing the underlid device underneath a lower eyelid, and supplying power to one or more of the plurality of stimulation electrodes. In some aspects, the underlid device is configured to remain entirely underneath the eyelid while in operation and being worn by a user.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIGS. 3A-3C present different views of an example underlid device, according to some aspects of the present disclosure.

FIG. 4 is a cross-sectional side view of a device placed between a lower eyelid and an eyeball, according to some aspects of the present disclosure.

FIGS. 5A and 5B present different views of an example underlid device, according to some aspects of the present disclosure.

FIG. 6 is a cross-sectional side view of a device placed between a lower eyelid and an eyeball, according to some aspects of the present disclosure.

FIGS. 13A-13C present different views of an example underlid device, according to some aspects of the present disclosure.

FIGS. 15A-15C present different views of a wand, according to some aspects of the present disclosure.

FIGS. 17A and 17B illustrate an example underlid device system in use, according to some aspects of the present disclosure.

FIG. 20 is an example method of operating an underlid device system, according to some aspects of the present disclosure.

DETAILED DESCRIPTION

Figure 1A:
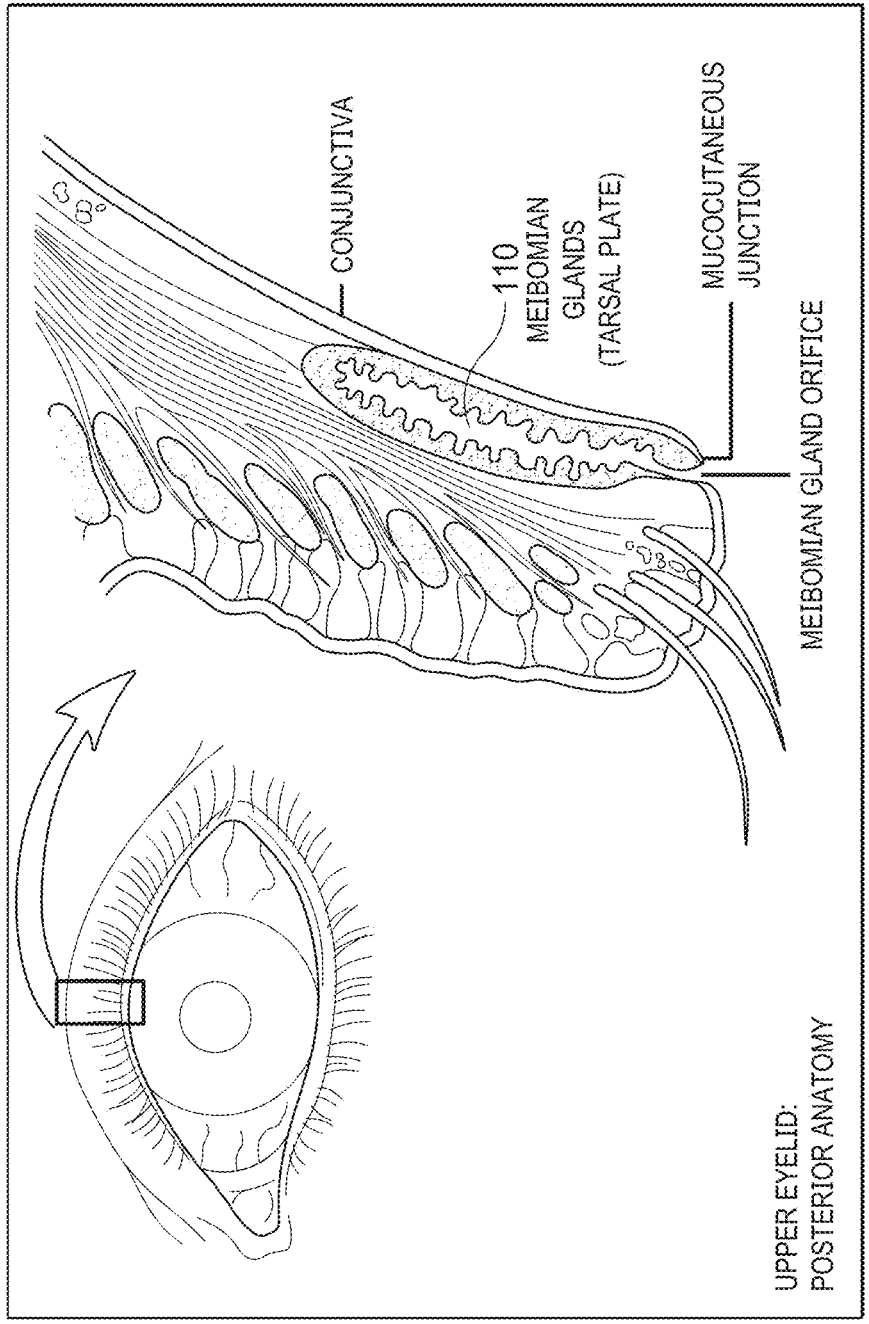
FIGS. 1A and 1B present different views of portions of one or more typical human eyelids, according to some aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1B:
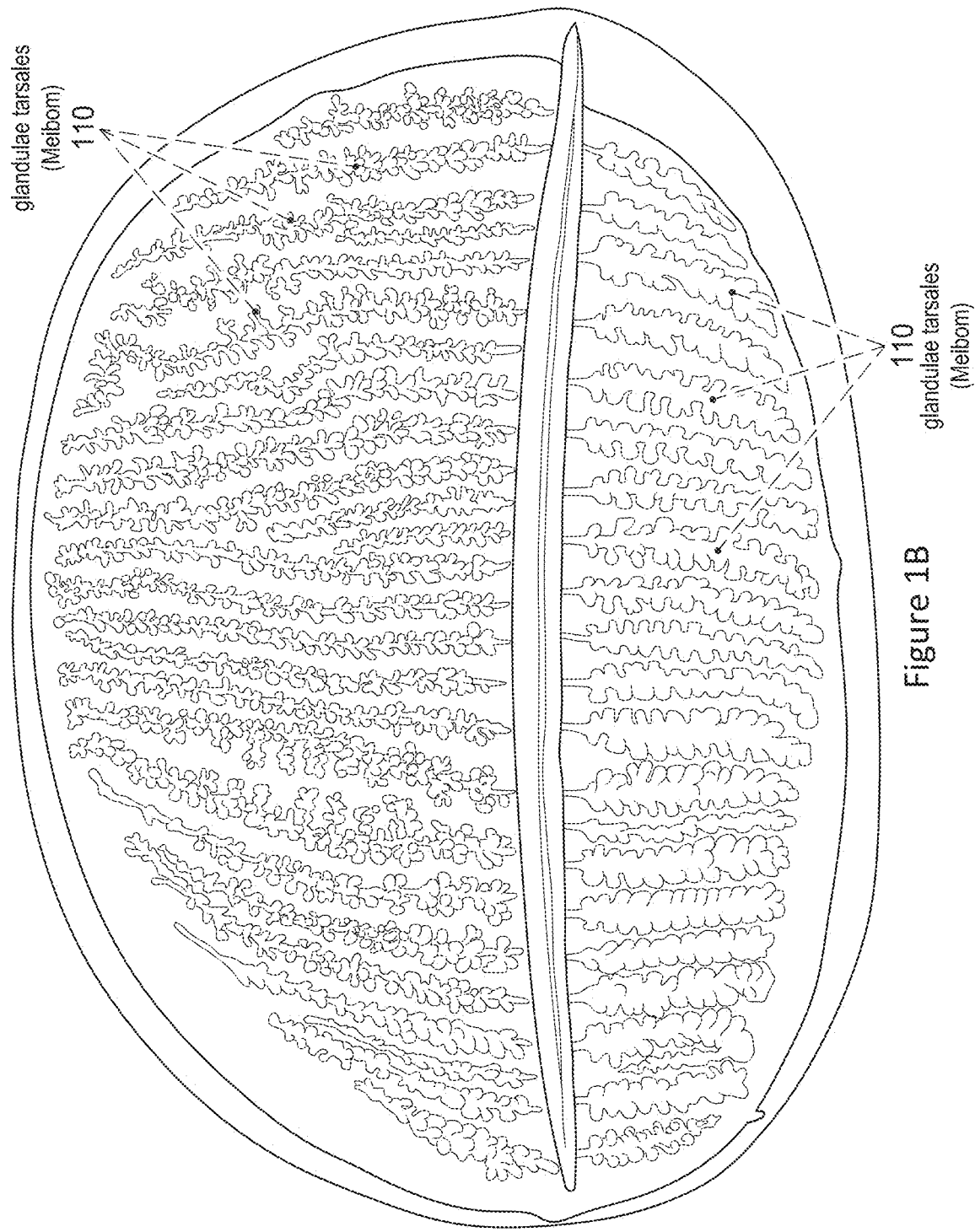

FIGS. 1A and 1B present different views of portions of one or more typical human eyelids. FIG. 1A illustrates a cross-sectional side view of an upper eyelid. An upper eyelid has a number of meibomian glands 110, one of which is shown in FIG. 1A and a number of which are shown in FIG. 1B.

Disclosed herein are devices for placement underneath the eyelid. The devices include one surface for facing the eyelid and another surface for facing the sclera. In some embodiments, the devices include electrodes configured to stimulate the sclera to induce a blink reflex and/or generate reflex tears. In some embodiments, the underlid devices include heating elements on the eyelid side to heat Meibomian glands in the eyelids to unclog glands and/or stimulate meibum. In some embodiments, the underlid devices further include magnetic materials responsive to an external magnet to engage the underlid device for massaging an eyelid and/or enhancing the heating of the eyelid. Underlid devices may include a combination of the aforementioned features.

Figure 2:
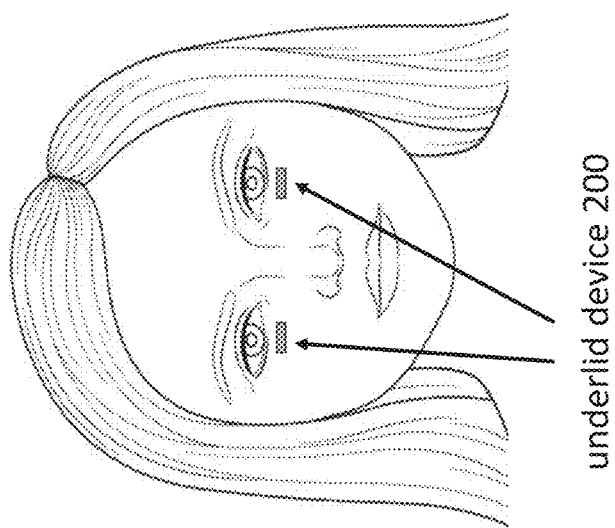
FIG. 2 illustrates the outline of a device as it resides underneath an eyelid, according to one positioning and embodiment of the device, according to some aspects of the present disclosure.

FIG. 2 illustrates examples of underlid devices 200. Each of the devices 200 is placed underneath an eyelid, and FIG. 2 illustrates the outline of each device 200 as it resides underneath each eyelid, according to one positioning and embodiment of the device 200. The devices 200 are designed to be worn by a user and to remain completely covered by an eyelid and underneath an eyelid, even when the eyelid is open as shown. In this embodiment, each device 200 is generally rectangularly shaped, but each device is not limited to this shape. The device 200 is configured to treat dry eye by applying heat to meibomian glands and/or applying a stimulation to the scleral and/or conjunctival surface as described further herein. As is well known, the sclera generally refers to the thick white layer that makes the white part of the eye while the conjunctiva generally refers to the thin layer that surrounds the entire eye except for the cornea. Heating meibomian glands assists with unclogging the glands so that oils within the glands flow onto the eye, and applying stimulation to the scleral and/or conjunctival surface assists with triggering the person to blink or produce reflex tears, each of which assist with treating dry eye disease. It is generally understood that discussion of stimulation of a sclera or scleral surface includes stimulation of a conjunctival surface overlaying the sclera.

The form factor of each device 200 is desirable relative to contact lenses because the device 200 covers substantially less surface area of the eye than a contact lens. Furthermore, a contact lens can aggravate dry eye because it interferes with the interaction between tears, oils produced by the meibomian glands and the eye itself. The device 200 does not have these drawbacks. Additionally, the device 200 beneficially is not in view of the user, so the device 200 does not negatively affect the user's eyesight in any way.

Figure 3A:
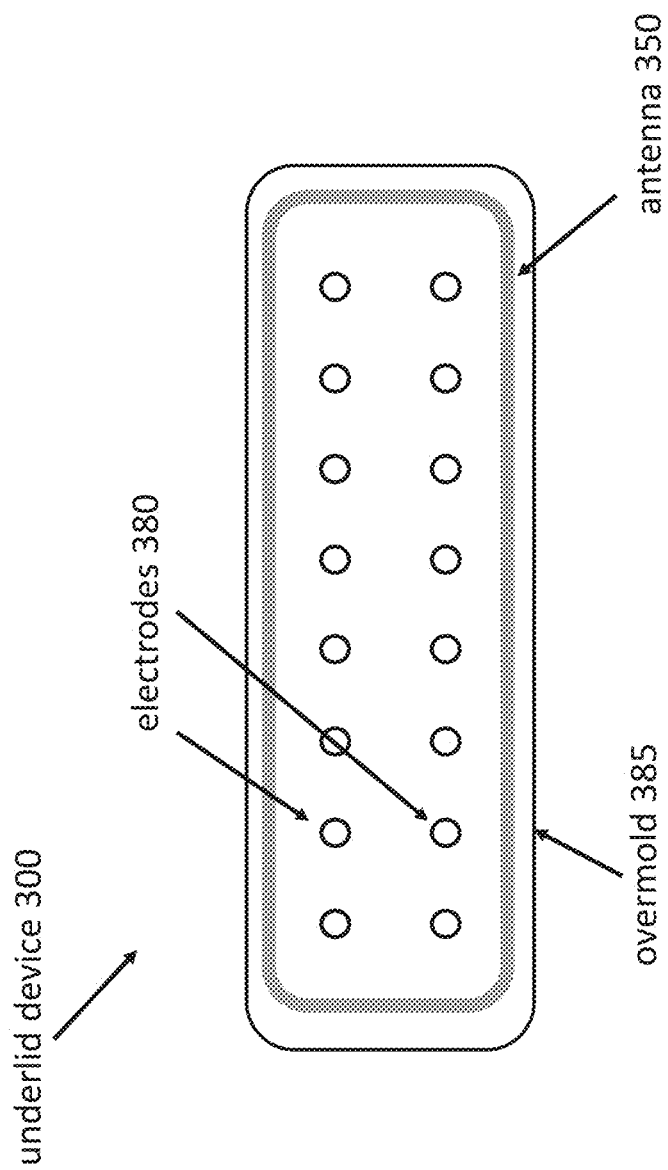

FIGS. 3A-3C present different views of an example underlid device 300, which is an example embodiment of device 200. FIG. 3A presents a view of a surface of the device 300 for opposing the sclera; FIG. 3B presents a view of an opposing surface of the device 300 for opposing an eyelid; and FIG. 3C presents a cross-sectional side view of the device 300. Generally, components shown in the view of the device 300 in FIG. 3A are used to stimulate a surface of the eye to stimulate blinking or reflex tears.

Beginning with FIG. 3A, the scleral side of device 310 includes a number of stimulation electrodes 380. The embodiment in FIG. 3B includes 16 stimulation electrodes 380 as an illustrative and non-limiting example. However, generally the device 310 includes two or more stimulation electrodes, or four or more stimulation electrodes. The electrodes 380 provide neurostimulation of cold receptors or nociceptors on the scleral surface to produce reflex tearing. The stimulation waveform is designed to stay below the pain threshold but still produce reflex tearing. The device 310 may be covered by a material 385, such as silicone elastomer or silicone hydrogel or Hydrogel, that is comfortable for a user when the device 310 is placed underneath, and against, an eyelid and against an eyeball. By using a plurality of electrodes, a patterned stimulation may be applied in which different electrodes or pairs or sets of electrodes are activated at different times to stimulate the sclera in different areas and orientations. The greater the number of electrodes, the greater the potential number of variations of stimulation patterns. In some embodiments, a periodic stimulation waveform is applied to the electrodes to generate blink rate.

As shown, the device 300 may also include an antenna 350. The antenna 350 as illustrated is configured as a loop antenna, but the antenna 350 generally can take any useful form for performing wireless charging via inductive wireless charging and/or for providing communications capability for the device 310. The antenna 350 may reside on a surface of the device 310 or may reside inside the device 310. The antenna 350 in this context may also be referred to as a wireless charging device. The wireless inductive charging occurs by coupling the antenna 350 to an external device that supplies energy to the device. The antenna 350 is coupled to the energy storage element 330 so that power received by the antenna is supplied to energy storage element 330 to charge energy storage element 330.

Turning to FIG. 3B, the device 300 may also include an integrated circuit (IC) 370 and/or an integrated passive device (IPD) 360. In an embodiment, the IC 370 is configured to provide any combination of the following: power management (such as managing the energy storage element 330 or energy harvesting via wireless charging), blink sensing, blink timing, or scleral/bulbar conjunctiva surface neurostimulation for tear production and/or stimulating the blink reflex. The electrodes 380 may be controlled by the IC 370 to produce any known type of neurostimulation waveform, such as a waveform utilizing any effective combination of pulse width, pulse frequency, pulse amplitude, duty cycle, on time, and/or off time, etc. Antenna 350 is located on a surface or inside device 310.

Device 300 additionally includes energy storage element 330, which stores energy for powering the device 300. Examples of energy storage element 330 are a battery and a capacitor. Device 300 additionally includes two electrodes 340. The electrodes 340 may be configured to sense the onset of a blink via, e.g., electromyography (EMG) or environmental impedance sensing to provide blink detection. For example, the electrodes may measure electric potential or voltage generated by a conjunctiva or other cells in the eyelid to detect the onset of a blink. The electrodes 340 may also, or alternatively, be configured to stimulate the eyelid muscles to cause a person to blink. For example, in some embodiments, IC 370 couples to electrodes 340 to provide both blink sensing and blink stimulation, taking one or more measurements from electrodes 340 to perform blink sensing and applying voltages or currents to electrodes to perform blink stimulation by stimulating the eyelid.

In some embodiments, the device width 316 is about 4 millimeters (mm), and the device length 318 is about 12 mm. In some embodiments, the energy storage element 330 is a 7.5 mF super capacitor with dimensions of about 3.2 mm×2.5 mm×0.9 mm, the integrated circuit 370 has dimensions of about 1.2 mm×1.2 mm×0.08 mm, and the IPD 360 has dimensions of about 1.0 mm×1.0 mm×0.08 mm. These dimensions are exemplary and not intended to be limiting.

Thus, the device 310 can be used to treat dry eye using electrodes 340 by performing blink stimulation, and/or treat dry eye using electrodes 380 to generate reflex tears or stimulate the eye surface to stimulate blinking.

Any pair of electrodes, such as electrodes 340, can be used to measure tear osmolarity based on an impedance measurement, such as using impedance spectroscopy. For example, the impedance measurement can be performed with a potentiostat circuit (at DC), or can be swept across frequency with a frequency-adjustable sine wave from one electrode, and analyzed through phase and magnitude through the return from the other electrode. By measuring tear impedance to determine osmolarity, the device 300 can implement closed-loop treatment of dry eye. For example, if impedance measurements indicate that the eye needs treatment, the device 300 can apply heating and/or stimulation as discussed herein. Measurements from the electrodes are supplied to a processor, such as integrated circuit 370, and the processor determines whether heating and/or stimulation should be applied based on the measurements. For example, if a measurement indicates that tear osmolarity exceeds a threshold, heating and/or electrode stimulation may be applied.

Turning to FIG. 3C, a cross-sectional side view of the device 300 is presented. Energy storage element 330, electrodes 380, and an overmold 385 are shown.

FIG. 4 is a cross-sectional view from the underside of the device 300 placed between a lower eyelid 420 and the sclera of an eyeball 430. In other words, FIG. 4 provides a cross-sectional perspective view of the device 300, a lower eyelid 420 and an eyeball 430 from underneath the device 300 when placed between the lower eyelid 420 and the eyeball 430. Consistent with the description above, the electrodes 380 are placed on the side facing the sclera 430.

Figure 5B:
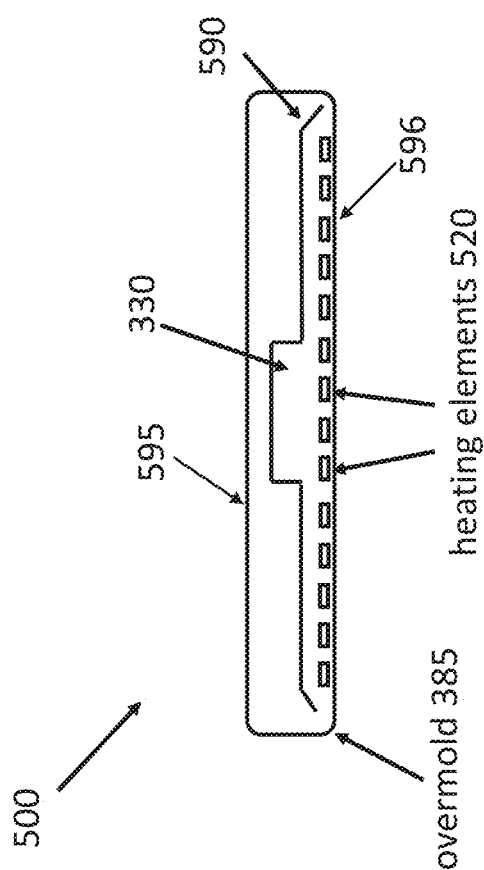

FIGS. 5A and 5B present different views of an example underlid device 500, according to some aspects of the present disclosure. Features of the device 500 that are the same as described previously utilize the same numbering and are generally not described further. The view of device 500 in FIG. 5A is from the perspective of the eyelid. In other words, FIG. 5A presents the eyelid facing portion of device 500. The device 500 includes a number of heating elements 520, examples of which are resistors or resistive heating elements. FIG. 5A presents one embodiment with 24 heating elements 520 for illustrative purposes, but generally any number of heating elements are included in underlid device 500. In some embodiments, the heating elements 520 are 100 ohm resistors.

Turning to FIG. 5B, a cross-sectional side view of the device 500 is presented. Energy storage element 330, heating elements 520, and an overmold 385 are shown. Additionally, a heat reflector 590, such as a Mylar heat reflector, is illustrated. The heat reflector 590 is designed to ensure the heat generated from resistive heating elements 520 does not cause harm to any portion of the human eye located on the opposing side of the device. The heat reflector 590 may form a layer within device 500 positioned between the heating elements 520 and a surface 595 configured to face a sclera of an eyeball. The heating elements 520 are positioned proximate to a second surface 596 of the device 500 configured to face an eyelid. The heating elements are positioned closer to the second surface 596 in order to facilitate heating of the eyelid. When power is supplied to heating elements 520, the temperature of the heating elements 520 is increased. Heating elements 520 facilitate heat transfer to eyelid tissue facing the heating elements 520. In some embodiments, power is supplied to heating elements 520 from energy storage element 330.

FIG. 6 is a cross-sectional view from the underside of the device 500 placed between a lower eyelid 420 and the sclera of an eyeball 430. In other words, FIG. 6 provides a cross-sectional perspective view of the device 500, a lower eyelid 420 and an eyeball 430 from underneath the device 500 when placed between the lower eyelid 420 and the eyeball 430. Consistent with the description above, the heating elements 520 are placed on the side facing the lower eyelid 420.

In some embodiments, underlid devices include heating elements but not electrodes, such as the device 500 illustrated in FIGS. 5A, 5B, and 6. In some embodiments, underlid devices include electrodes but not heating elements, such as the device 300 illustrated in FIGS. 3A-3C and 4. Depending on the desired application, underlid devices can be configured to provide only heating of meibomian glands using heating elements or only stimulation of the eye surface using electrodes. In some embodiments, underlid devices may include both electrodes and heating elements. Such a device is illustrated in FIG. 7.

Figure 7:
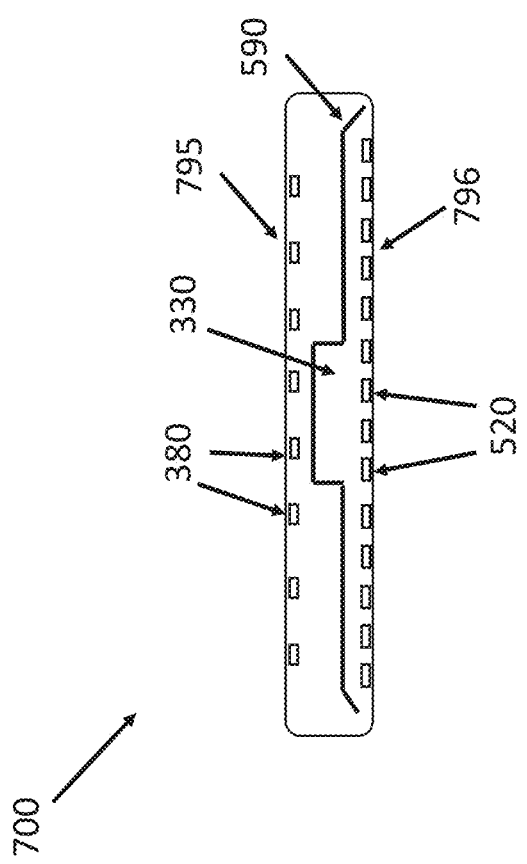
FIG. 7 is a cross-sectional side view of a device according to some aspects of the present disclosure.

FIG. 7 is a cross-sectional side view of a device 700 according to some aspects of the present disclosure. Features of the device 500 that are the same as described previously utilize the same numbering and are generally not described further. Device 700 includes electrodes 380, heating elements 520, and a heat reflector 590, such as a Mylar heat reflector. The device includes a first surface configured to face an eyeball and a second surface configured to face an eyelid. A cross-section of the first surface is indicated as 795 in FIG. 7, and a cross-section of the second surface is indicated as 796.

Figure 8:
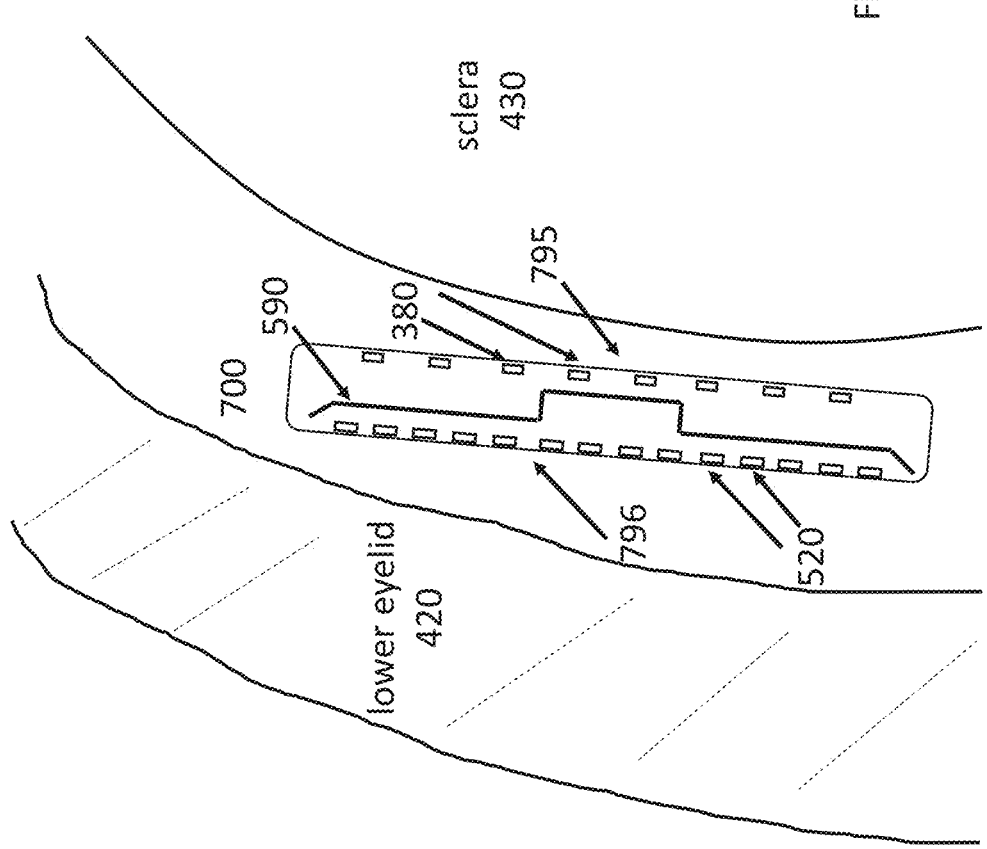
FIG. 8 is a cross-sectional side view of a device placed between a lower eyelid and an eyeball, according to some aspects of the present disclosure.

FIG. 8 is a cross-sectional view from the underside of the device 700 placed between a lower eyelid 420 and the sclera of an eyeball 430. In other words, FIG. 7 provides a cross-sectional perspective view of the device 700, a lower eyelid 420 and an eyeball 430 from underneath the device 700 when placed between the lower eyelid 420 and the eyeball 430. Consistent with the description above, the heating elements 520 are placed on the side of the device 700 facing the lower eyelid 420, and the electrodes are placed on the side of the device 700 facing the sclera 430.

Figure 9:
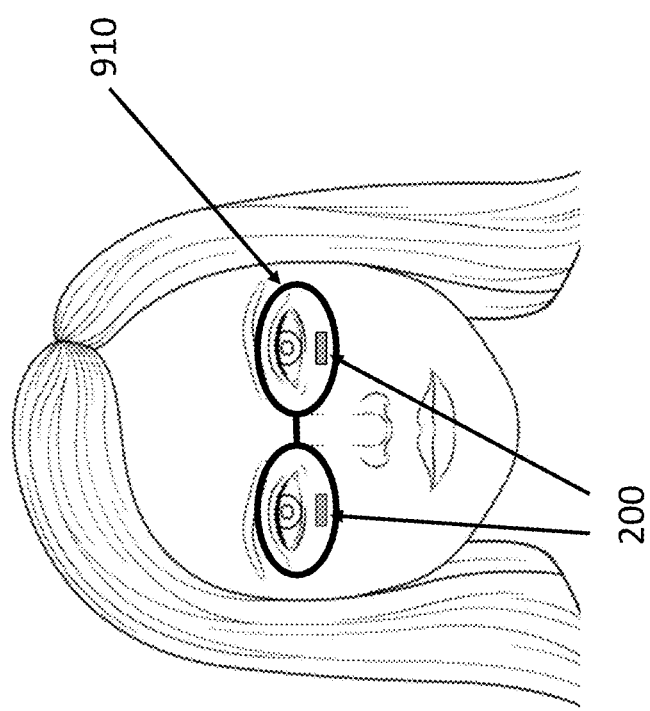
FIG. 9 illustrates the outline of a device as it resides underneath an eyelid together with an external device, according to one positioning and embodiment of the underlid device, according to some aspects of the present disclosure.

There are various potential use cases for underlid devices, such as those described herein. In one use case, the devices 200 are used together with an eyeglasses form factor 910, such as illustrated in FIG. 9. As shown in FIG. 9, an underlid device 200, such as devices 300, 500, or 700 described previously, is placed underneath each eyelid of a person as shown. The outline of underlid devices 200 positioned underneath a person's eyelid are shown. The devices 200, such as devices 300, 500, or 700, are designed to be worn by a user and to remain completely covered by an eyelid and underneath an eyelid, even when the eyelid is open as shown.

The person also wears an associated eyeglass frame 910. The frame 910 may include portions that reside over a person's ear (not shown), and the frame 910 may or may not include glass eyepieces. The frame 910 may be any sort of known eyeglass frame form factor. FIG. 5 thus illustrates a system for stimulating the human eye including one or more devices 200 and frame 910.

However, the frame 910 may also contain electronics for operating the devices 200. For example, the frame 910 may include a power transfer and communications coil, such as an antenna, for wirelessly coupling to a coil or antenna, such as antenna 350 discussed previously. Blink detection may be performed by the frame 910 via inward-facing infrared reflectometer or camera and communicated to the underlid device or using EMG or environmental impedance sensing electrodes on the underlid device 200 itself. The underlid devices 200 may or may not include energy storage elements, as energy for stimulation and/or heating may be supplied by the frame 910. If the underlid devices 200 include energy storage elements, the frame 910 may charge the energy storage elements and/or supply energy as needed to the underlid devices.

Each device 200 may perform blink sensing and energy harvesting monitoring. If there is sufficient power harvesting, and a blink is detected, the device 200 can activate the heating, via resistive heating elements, so that the heating can occur in sync with the eyelid blink. One reason to synchronize the heat with the blink is that due to limited power available to do the heating, the heat application works well to melt the waxy/oily lipid layer and "de-clog" the meibomian glands. The motion of a blink works naturally to eject meibum oil from the meibomian glands.

Instead of detecting when the blink occurs, in other embodiments, the electrodes on the eyelid side are utilized to stimulate the eyelid muscles prior to heat application to suggest, stimulate, or encourage a blink during heating. In some embodiments, an on-chip timer in the device 200 is utilized to make sure this does not happen too often or too slowly (use the same electrodes to sense average blink rate over a long time, when there is still insufficient harvested power to do a stimulation event). In addition or alternatively, a scleral side may be periodically stimulated via stimulation electrodes to cause natural tear production.

Figure 10:
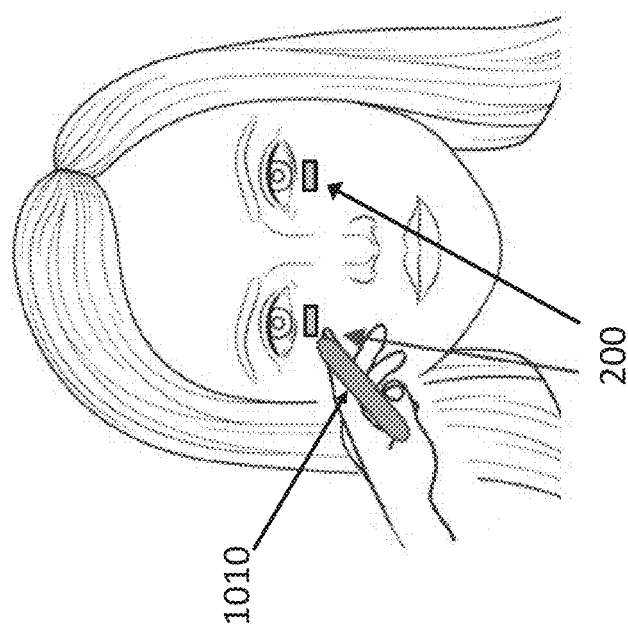
FIG. 10 illustrates the outline of a device as it resides underneath an eyelid together with an external device, according to one positioning and embodiment of the underlid device, according to some aspects of the present disclosure.

A second use case for devices 200 is presented in FIG. 10. This use case involves a system including one or more devices 200, such as devices 300, 500, or 700 described previously, and handheld wand 1010. Instead of a wand 1010, the system may instead use a glove or finger cot. Regardless of whether a wand 1010 or glove or finger cot is used, each of which may be referred to as an external device, the external device in some embodiments includes a wireless power transfer coil at a fingertip to provide enough power to heat device 200 via resistive heating elements as discussed herein and also for communication with device 200.

Buttons on the external device, such as device 1010, can be easily operated by the thumb to enable/disable heating, and/or to enable scleral stimulation for tear production. When the user feels his/her eyes are dry, he/she can bring the external device, such as device 1010, on the other side of where the underlid device 200 is installed, and they can gently massage their eyelid. At the same time, they can also hold a button down on the external device, such as device 1010, to enable heating. Because the distance between the power transfer coil on the external device and the underlid device is small, a lot of power can be transmitted for continuous heating. The continuous heating can happen during the entire time the user is massaging their eyelid to help mechanically and thermally stimulate the meibomian glands. As needed, the user may also press a button on the external device 1010 to cause the underlid device 200 to stimulate the scleral surface to generate tears.

In yet a third use case, underlid device 200 includes an energy storage element sufficient to power the device 200 for continuous operation over a relatively long period of time (e.g., days or weeks) and does not require any external device to provide power or control for such operation. For example, the energy storage element in underlid device 200 may be a battery. In such embodiments that do not require an external device, the underlid device 200 includes a processing unit, such as a processor or IC, configured to initialize heating using heating elements or initialize neurostimulation using electrodes according to a predefined schedule or criteria. The underlid device 200 in this third use case may be removed from underneath the eyelid and placed in a charging device for charging the energy storage element before being placed back underneath the eyelid. In this manner, the underlid device 200 may be used repeatedly over many days.

Figure 11A:
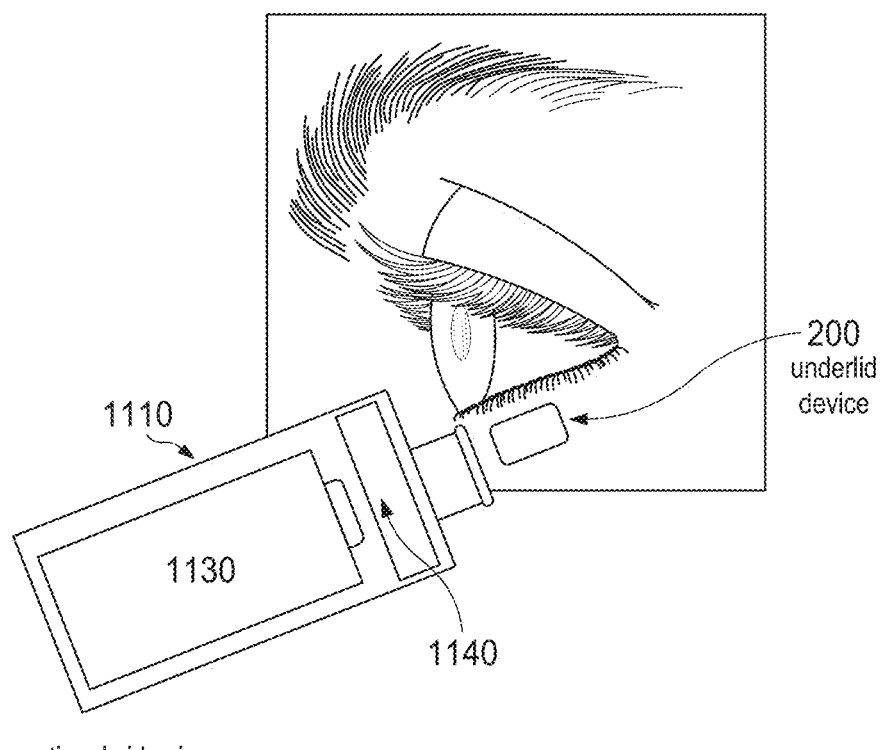
FIGS. 11A and 11B present an example underlid device system in use, according to some aspects of the present disclosure.
Figure 11B:
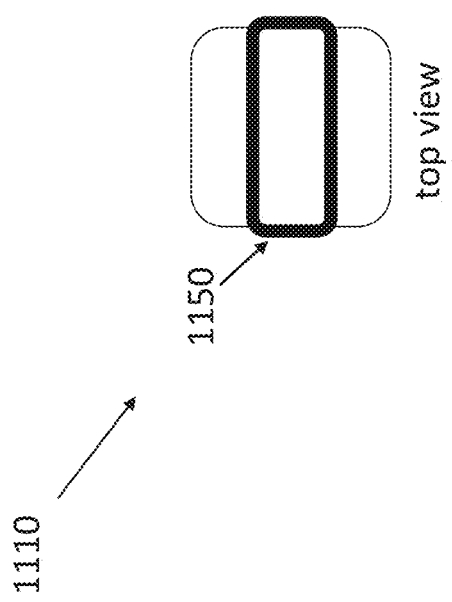

FIGS. 11A and 11B presents an example underlid device system in use, according to an embodiment. The underlid device system includes an underlid device 200 and an external device 1110 (or device external to the human user). FIG. 11A is a perspective view of an underlid device 200 and external device 1110, and FIG. 11B is a top view of the external device 1110. FIG. 11A illustrates one potential electromagnetic coupling between the underlid device 200 and external device 1110. Each device utilizes an antenna 750, which can be used for wireless charging of underlid device 200 and communication between devices 1110 and 200. As shown, external device 1110 includes an energy storage component 1130, used to provide power to underlid device 200. The energy storage component may be a battery, such as a rechargeable battery. In this embodiment, external device 1110 includes electronics 1140, including a processing unit such as an IC or processor for controlling external device 1110. In some embodiments, the electronics 1140 may also include a memory for storing instructions to be executed by the processing unit.

Figure 12:
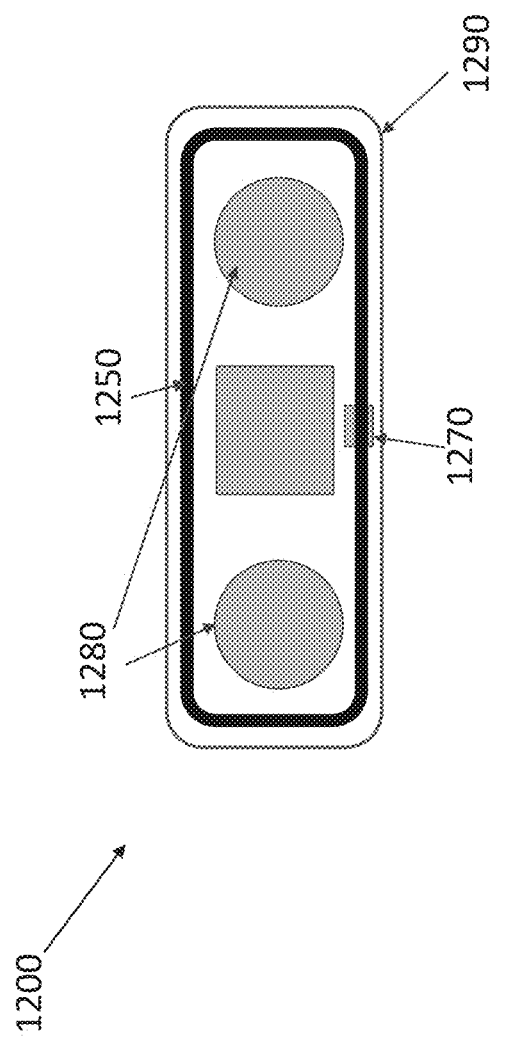
FIG. 12 presents a view of an example underlid device, according to some aspects of the present disclosure.

FIG. 12 illustrates an underlid device 1200 that performs blink detection and closed-loop blink stimulation. The device 1200 includes a pair of electrodes 1280, an antenna 1250, and an IC 1270 for wireless power, communications, power management, stimulation, and estimation of tear film osmolarity through wideband impedance spectroscopy measurement. The device also may include a super capacitor for energy storage to power the device 1210. The pair of electrodes 1280 are used to estimate tear film osmolarity through wideband impedance spectroscopy measurement. The pair of electrodes 1280 is also used to stimulate blinking. The device 1210 is configured to be placed on top of the eyeball and underneath a lower eyelid in a human patient. The electrodes 1280 may face the eyeball surface or they may face the eyelid surface.

Figure 13A:
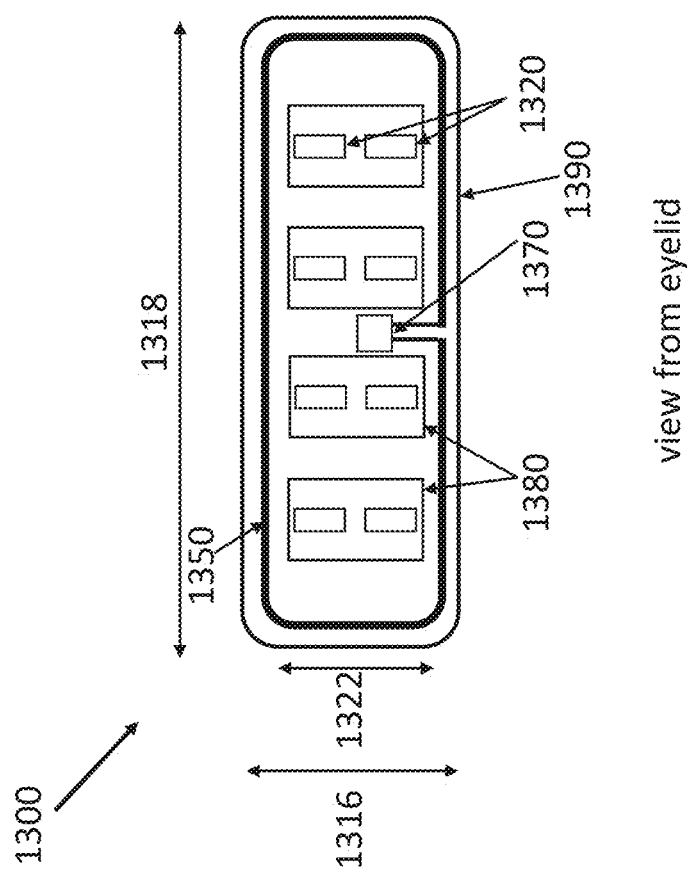

FIGS. 13A-13C present three perspective views of another embodiment of an underlid device 1300. FIG. 13A presents a view of components on a front, or anterior, side of the underlid device 1300, which is configured to be positioned against an eyelid. FIG. 13B presents a view of components on a backside, or back, or posterior, side of the underlid device 1300, which is configured to be placed facing a surface of an eye. FIG. 13C presents a cross-sectional side view of the underlid device 1300. Example dimensions are a length 1318 of about 12 mm and a width of about 4 mm, but other dimensions are contemplated by this disclosure.

As illustrated, device 1300 in FIG. 13A includes an antenna 1350 for wireless charging and/or communication, eight heating elements 1320, four magnetic stacks 1380, an integrated circuit 1350, and an overmold 1390. The number of heating elements 1320 and magnetic stacks 1380 is merely exemplary, and any number of those elements may be used. The integrated circuit 1350 may be used for, among other functions, power rectification, power distribution to heating elements 1320, and/or temperature sensing for safety (utilizing temperature probes located either on the eyelid side of FIG. 13A or the sclera side in FIG. 13B). FIG. 13B illustrates features of device 1300 as seen from the eyeball side. The overmold may be made of SiHy and form a moisture barrier.

Figure 14:
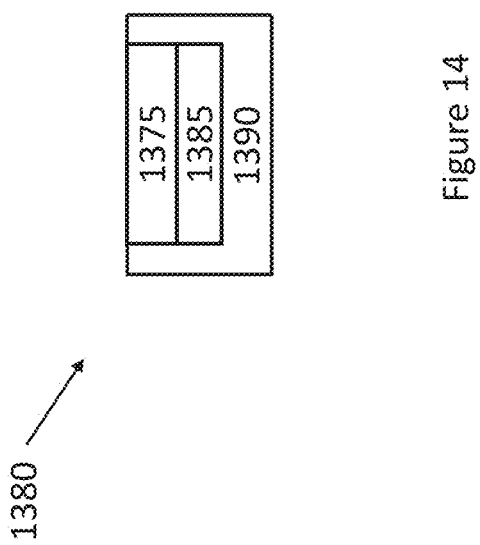
FIG. 14 is a cross-section of a heat reflective and insulating stack, according to some aspects of the present disclosure.

An embodiment of magnetic stack 1380 is illustrated in FIG. 14. Magnetic stack 1380 includes a thermal heat shield 1375, magnetic material 1385, and an insulating material 1390, such as an aerogel. The thermal heat shield 1375 helps keep the heat directed to the eyelid from reaching the sclera. Examples of magnetic material 1385 are a high ferromagnetic metal or magnet.

FIG. 13C illustrates a cross-sectional view of device 1300. The device 1300 optionally includes trenches, such as trench 1395, molded into the underlid device 1300 around the heating elements 1320 to help increase local pressure and/or assist with heat transfer into the eyelid.

An underlid device, such as the device 1300 illustrated in FIG. 13A-13C, can have any combination of the following characteristics. The underlid device avoids anesthetization of the eye surface (required of other prior art techniques) so that their device can cover the eye. An underlid device may use radio frequency (RF) energy harvesting for converting energy to resistive heating. An underlid device may employ a special magnetic-sensitive stack or stackup that responds to external magnetic fields (with a permanent magnet or ferromagnetic material) such that the eyelid is squeezed between an external handheld stimulator and the underlid device. This stackup also contains materials to reflect, shield, and insulate the heat coming from the resistive heating from getting to the scleral surface. The underlid device may also include trenches, "dimples," chevrons, or other relevant features that can increase the local pressure around the features to help excavate the Meibomian glands of meibum, as the underlid device is moved around or pulsed by the magnetic field and external handheld stimulator movement while the electromagnet in the handheld device is energized. The underlid device may also include safety features, such as tracking underlid temperature for protection.

Figure 15B:
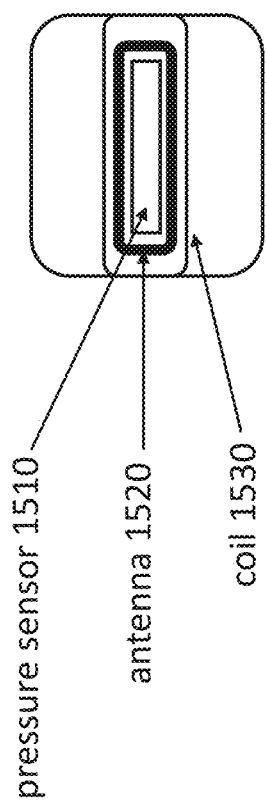

Devices, such as the device 1300 presented in FIGS. 13A-13C, can be designed to be used in conjunction with a wand, which may be of a size to be handheld. FIGS. 15A-15C illustrate different views of an example embodiment of a wand 1500 to be used together with an underlid device, such as device 1300. The wand 1500 may also be referred to as a handheld stimulator. A dimension 1518 of wand 1500 may be about 14 mm, although any width may be used. A dimension 1516 of wand may be about 6 mm, although any width may be used.

The wand 1500 includes a pressure sensor 1510, an antenna 1520, a coil 1530, electronics 1540, an energy storage device 1550, such as a battery or capacitor, and a user interface 1560. The antenna 1520 may be used for receiving power delivered by induction for wireless charging and/or wireless communication. The pressure sensor 1510 may be used to detect application of the wand 1500 to a user's skin. The coil 1530 may include a ferrite core to enhance the use of coil 1530 as an electromagnet. In an embodiment, the electronics 1540 may include an integrated circuit or other type of processor to control delivery of power to the device 1500, wireless communications, and/or magnetizing the coil 1530. The user interface 1560 may be utilized by the user to control positioning or activation of an underlid device. For example, the user interface 1560 may include buttons or an electronic touch display to allow a user to control or activate electronic stimulation, thermal stimulation, or mechanical stimulation (as discussed later) of an underlid device.

Wands, such as the wand 1500 shown in FIGS. 15A-15C, can have any combination of the following characteristics. The wand may include a wirewound electromagnet that is supplied by a switchable DC current source; a power transfer antenna that is supplied by an adjustable RF (AC) source; and/or buttons and knobs that allow the user to set amplitude, pulse, and other parameters that will deliver therapeutic heating and mechanical stimulation modes, as needed or desired. The wand may also or alternatively include safety features and/or treatment tracking, by tracking motion of the wand, time of treatment, duration of treatment, frequency of treatment, and/or effectiveness of treatment. The wand may also or alternatively include a pressure sensor to track applied force. Such a pressure sensor may be used to provide an indication of when, and for what duration, treatment is applied.

Figure 16:
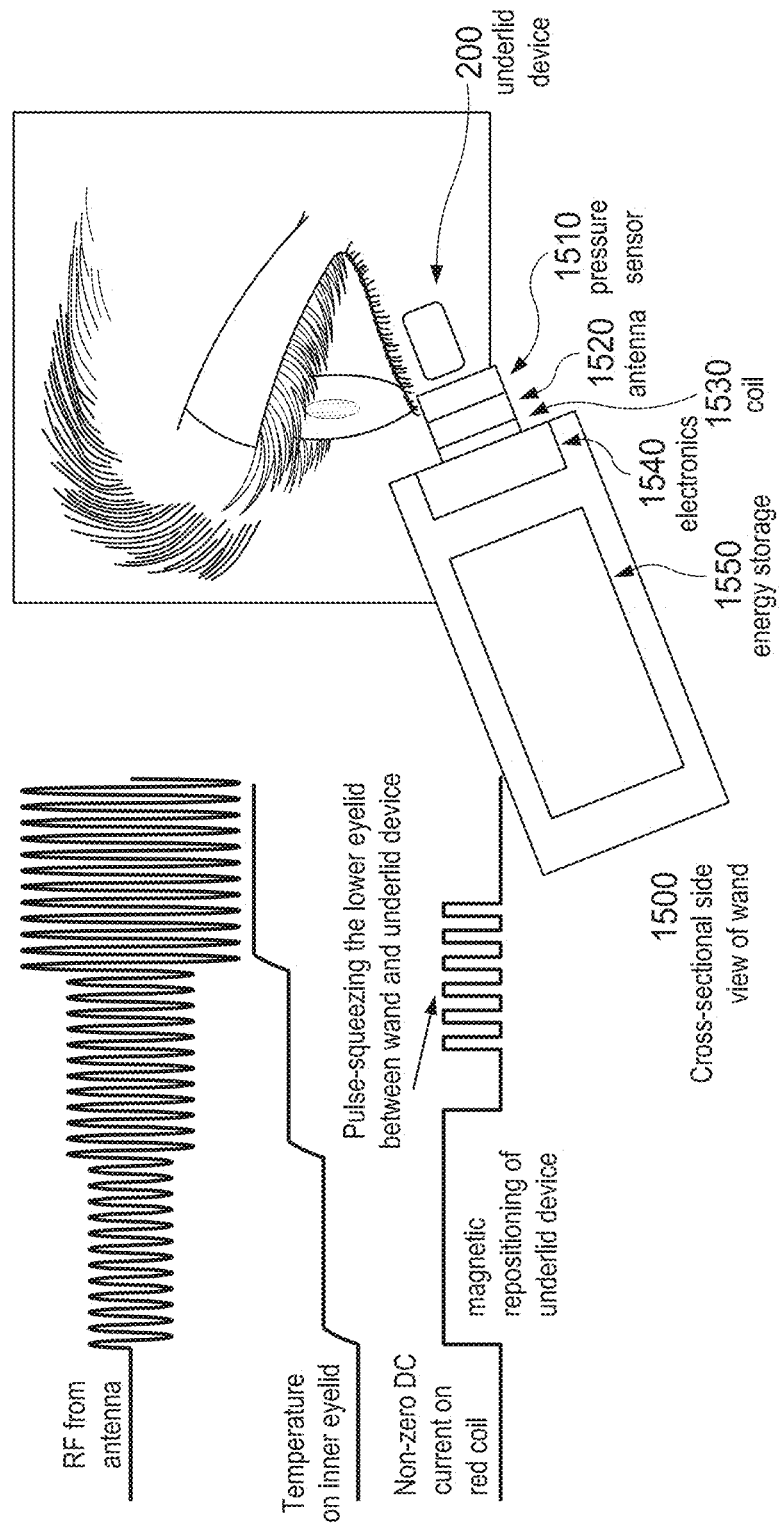
FIG. 16 explains and presents an example underlid device system in use, according to some aspects of the present disclosure.

FIG. 16 illustrates an underlid device system, which includes an underlid device 200, such as any underlid device described herein, in use. The underlid device system includes a stimulation wand 1500 as shown and an underlid device 200 positioned underneath an eyelid. FIG. 16 illustrates a cross-sectional side view of wand 1500.

FIG. 16 illustrates an example embodiment of waveforms used during operation of the stimulation wand as well as a corresponding example temperature response of the inner eyelid during operation. An electromagnetic coil 1530 in the wand 1500 is selectively magnetized to engage the underlid device to assist in moving the device. This is illustrated as "magnetic repositioning of underlid device" in FIG. 16. Energy from the signal propagated by RF antenna is utilized to power the resistive elements to heat Meibomian glands in the eyelid. FIG. 16 shows one such signal from the RF antenna of the wand and an example resulting temperature of the inner eyelid as a result of the signal being received by the underlid device. An electromagnetic coil 1530 in the wand 1500 is magnetized in a pulsed manner to alternately squeeze and release the underlid device 200 against the eyelid.

The wand 1500 may utilize various safety features or systems for safety. Magnetic force may be sensed by pressure sensor 1510 to limit the magnetic force. Temperature may be sensed and a heating limit applied using an integrated circuit in electronics 1530. Furthermore, operating radio frequency (RF) antenna 1520 and coil 1530 can coexist, as the RF antenna 1520 runs on alternating current (AC), and the coil 1530 utilizes direct current (DC).

FIG. 17A illustrates an example underlid device system before repositioning of the underlid device 200, and FIG. 17B illustrates the underlid device system after repositioning of the underlid device 200. Repositioning is accomplished via use of an electromagnet in the illustrated wand 1500. A DC current is applied to a coil in the wand as shown to magnetize the electromagnet and engage the underlid device. After using the electromagnet to reposition the underlid device, the electromagnet can be used to stimulate the underlid device to stimulate the eyelid by alternately squeezing and relaxing the eyelid. Pulsed square waves in the waveform in FIG. 17B are an example waveform to achieve such stimulation of the eyelid, although other waveforms may be used.

Firmly pressing, massaging or squeezing the lower eyelid, such as shown in FIG. 17B, has the following characteristics and/or benefits. First, forces are concentrated on expressing the Meibomian glands. Second, excess pressure is not placed on the eyeball. Third, frequency and pulse amplitude may be controlled by a wand or other external device. Fourth, a pressure sensor in a wand or other external device can be used to measure pressure. Fifth, the squeezing force that can be generated between a ferromagnetic material in an underlid device and a magnet, such as an electro-magnet in a wand or other external device, depends primarily on area of the ferromagnetic material in contact with the eyelids, not on volume of the ferromagnetic material.

An example electromagnet design for the stimulation wand has the following design parameters. A roughly 1.4 Tesla electromagnet provides sufficient squeezing force between a 3 mm typical eyelid thickness. The following are used in an example embodiment: a soft iron core with 5K relative magnetic permeability; 36 gauge magnet wire that gives about 100 turns per inch and 400 ohms/foot of resistance. A design includes a 1-inch long electromagnet with a ⅜ inch wide head that has a length of about 157 inches or 13 feet (providing a resistance of roughly 5 ohms). At a current of 0.2 A this design leads to a voltage drop of 1 volt and about 2.5 T magnetic field.

Figure 18:
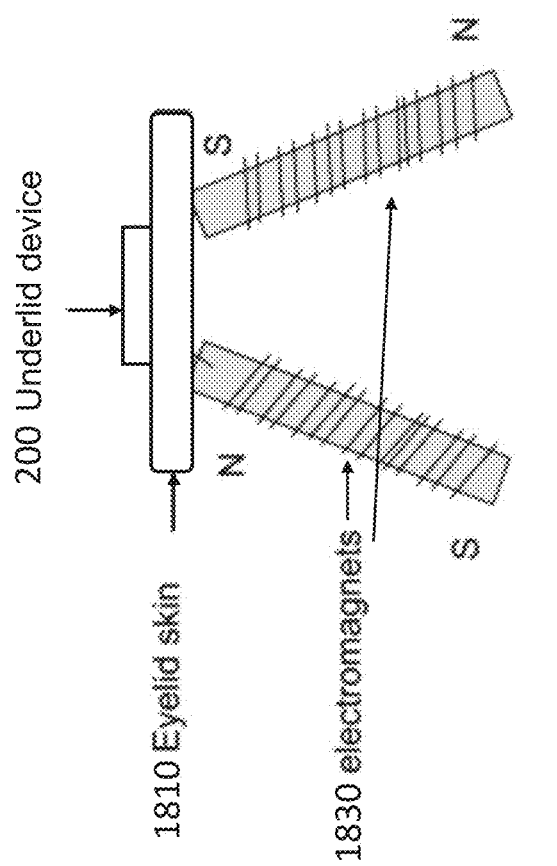
FIG. 18 presents principles of how an underlid device system operates, according to some aspects of the present disclosure.

FIG. 18 illustrates example electromagnets 1830 engaging a magnetic underlid device 200 when the underlid device is positioned underneath an eyelid 1810. A maximal field coupling and magnetic field gradient creates lateral forces on the underlid device 200 to lock its lateral position into place.

Some examples of smart stimulation wand features and functionality are as follows: form factor—whiteboard marker size; outer underlid contact surface—antimicrobial; connectivity—Bluetooth to smartphone app. A handheld wand, such as wand 1500, may include a variety of stimulation waveforms for magnetic pulsing and algorithms. A handheld wand may include various treatment tracking features, such as an accelerometer to track wand's treatment motion, and/or a wireless connection with a cellphone to give better treatment advice (figure out where "blindspots" are in treatment and suggest to user where they should spend more time), or not staying enough time in one spot. The handheld wand may track treatment time(s) and duration, and send reminders. The handheld wand may utilize a pressure sensor on wand tip to get an idea of force applied (protection as well as data). An underlid device utilized with a handheld wand may utilize thermal stimulation, for example, to melt the meibum that is clogging Meibomian glands. Such an underlid device may additionally or alternatively employ mechanical stimulation to provide a DC and pulsed magnetic field for an eyelid squeezing motion, as well as ability to move the underlid device around.

The following is a usage example of an underlid device system.
1. Insert underlid device in the upper or lower (can be either, to treat MGD) underlid region.
2. Bring wand close to the underlid region on the outside.
3. Enable the RF on the wand to engage heating. The circuits in the underlid device may detect temperature on the eyelid surface (heating surface) as well as the eyeball surface and ensure the operation is within the safety range.
4. Pulse the electro-magnet with an AC current on the wand to start pulsing/squeezing. The pressure sensor on the tip of the wand will ensure no excessive force will be applied to the eyelid due to excessive current driving the electro-magnet.
5. Enable the electro-magnet with a dc current on the wand to "grab" onto the underlid device and sandwich the eyelid
6. Slide the underlid device around with the electromagnet engaged to mechanically stimulate meibomian glands in a "wiping" motion, and to move the underlid device to another treatment area.
7. Throughout this entire treatment time, the wand will be tracking the wand motion and keep track of where the underlid is being treated, and how much time each section (and what kind of thermal and mechanical stimulation) each section of the underlid is getting treated. Via bluetooth connection and smartphone app, the device will give useful feedback & coaching to the user as to which areas have been sufficiently treated, and what other areas need more treatment of a certain nature (i.e.—wiping through, or pulsed action, or more heat, etc.)
8. A smartphone application can send reminders to the user for follow up treatments, and may also send push notifications to ask the user caring questions related to their dry eye disease and treatment regimen such that the treatment becomes proactive instead of reactive.

Figure 19:
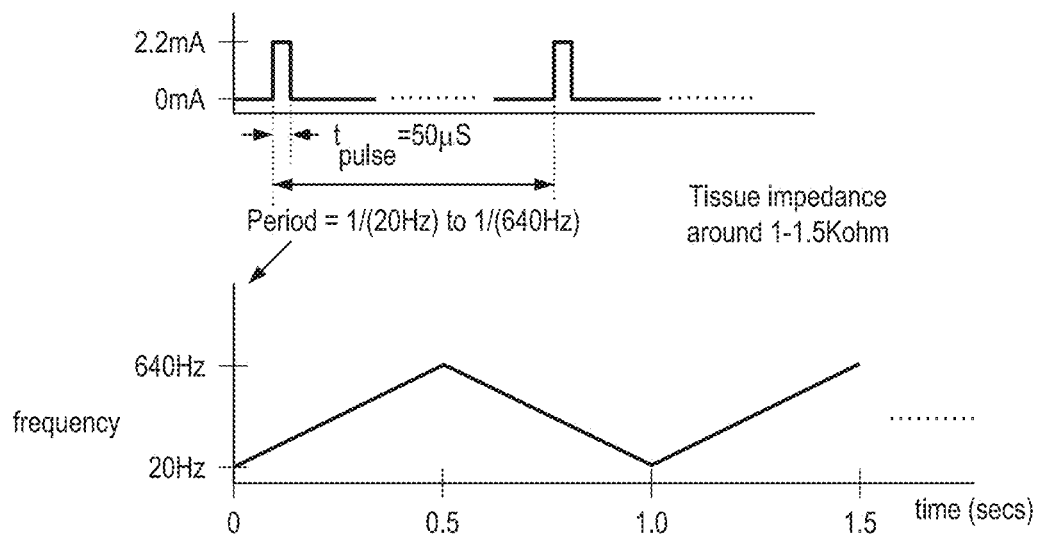
FIG. 19 presents an example stimulation waveform, according to some aspects of the present disclosure.

As explained earlier, the electrodes in an underlid device may be controlled by an integrated circuit or other processor to produce any known type of neurostimulation waveform, such as a waveform utilizing any effective combination of pulse width, pulse frequency, pulse amplitude, duty cycle, on time, and/or off time, etc. FIG. 19 presents an example neurostimulation waveform, according to some aspects of the present disclosure. The waveform may be applied via electrodes in any of the underlid devices having stimulation electrodes presented herein.

As shown in FIG. 19, an example waveform has a pulse width of 50 µs (microseconds), although pulse widths up to 250 µs may be used in this example. The pulses are applied with a period of between 20 Hz and 640 Hz, meaning the time between the beginning of each pulse is about 1/(20 Hz) and 1/(640 Hz). The frequency versus time of an example stimulation pulse is indicated in FIG. 19. The stimulation signal is a frequency chirp signal whose frequency increases over a time period followed by decreasing over a time period in repeating cycles. As shown, the frequency increases linearly from 20 Hz to 640 Hz in 0.5 s and then decreases linearly from 20 Hz to 640 Hz in the next 0.5 s, followed by a repeating cycle. This disclosure recognizes neuroreceptors among different people may have different resonant frequencies, or frequencies of stimulation that are effective to induce tear production. By sweeping across pulse frequencies at a moderate rate, a frequency chirp signal can be used across populations, without the need for tuning or calibration to find each person's particular neural resonant frequency. In some embodiments, a processor (such as IC 370) in devices 200, 300, 500, 700, and/or 1300 is configured to control a supply of power from an energy storage element (such as energy storage element 330) to apply a chirp stimulation signal to various sets of electrodes in those devices for stimulating the sclera and/or conjunctiva.

As shown in FIG. 19, the pulses may be monophasic pulses, but biphasic pulses may instead be used. Low pulse widths may be utilized to help promote targeting of nerve cells that promote tearing, while avoiding the simulation of other types of neuroreceptors.

FIG. 20 illustrates a method 1900 for treating dry eye symptoms using an underlid device, such as any of the underlid devices presented herein, for example, devices 200, 300, 500, 700, or 1300. The method 1900 commences in step 1910. In step 1910, an underlid device, such as the embodiments of underlid devices described previously, is positioned underneath an eyelid of a patient. For example, an underlid device is placed between an eyelid and eyeball as shown in FIG. 4, 6, 8 or other figures herein. Once positioned, in step 1920 a determination is made whether a condition is satisfied. Step 1920 is an optional step that may not be employed. For example, the method 1900 may go from step 1910 directly to step 1930, wherein a treatment is applied.

Returning to step 1920, a condition may be detected by sensors in the underlid device. According to one embodiment, the sensors may include a pair of electrodes, such as electrodes 340 in FIG. 5A, and the electrodes are used to measure tear film conductance or impedance, which can be used to provide a measure of tear osmolarity as discussed herein. In one embodiment, if the tear osmolarity exceeds a threshold, thereby signaling a dry eye condition, the condition in step 1120 is satisfied and a treatment is applied in step 1930, thereby providing relief to or treating the dry eye condition. In some embodiments, the treatment includes supplying power to various electrodes, such as electrodes 380, to stimulate a sclera to produce reflex blinking or reflex tear production. In some embodiments, the treatment includes supplying power to various heating elements, such as heating elements 520, to heat Meibomian glands in the eyelid to stimulate meibum production and/or unclog glands to relieve dry eye. In some embodiments, the treatment includes both stimulating the sclera and heating Meibomian glands using an underlid device such as illustrated in FIGS. 7 and 8.

In some embodiments, the treatment in step 1930 includes utilizing an external device, such as a handheld wand. An example wand is illustrated as wand 1500 herein. The external device is utilized to engage an underlid device that includes magnetic material. An example underlid device with magnetic material is presented in FIGS. 13A-13C. The treatment includes the wand generating magnetic pulses to alternately squeeze and release the eyelid between the wand and an underlid device. The magnetic pulses may be periodic or aperiodic. This alternate squeeze and release action massages the Meibomian glands to unclog the glands and/or stimulate meibum production. The treatment may also include supplying power to heating elements in the underlid device to apply heat to the Meibomian glands and/or supplying power to electrodes to stimulate a blink or reflex tears. The electrodes may face either the eyelid or the sclera.

During operation, an underlid device may utilize electrodes or other sensors for blink detection. By detecting blinks and keeping track of the time between blinks, the underlid device can compute a blink rate over a predetermined time interval. In an embodiment, the blink rate is computed as the number of detected blinks in a time interval. The blink rate may be used as a condition in step 1920. For example, if the blink rate is too low, the method 1900 moves to step 1930 in which power is supplied to electrodes to stimulate one or more blinks and increase the blink rate to an acceptable level.

In step 1940, the underlid device is removed from between an eyelid and eyeball. The underlid device may be removed for cleaning, charging an energy storage element, or replacement or disposal, as examples.

The devices and systems described herein can be safely used at home and provide invisible therapy options in a background, or on-demand (acute treatment) method. This system may also gather eye position and blink rate data for other data-driven diagnostics. Localized, protected heating through an underlid device does not require invasiveness or anesthetic to be applied as in other prior art systems, and allows for home-based application. Two different secondary hardware devices (frames or handheld external device) allow for two distinct therapy strategies to be applied with the same underlid device: background, continuously applied therapy, or on-demand, manual therapy (acute treatment).

Persons skilled in the art will recognize that the devices, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A device configured to be located underneath an eyelid, positioned between the eyelid and a surface of an eye, and worn by a user for treating a medical condition, the device comprising:
   a first surface configured to face a portion of a sclera of the eye and to be in contact with the surface of the eye;
   a second surface configured to be in contact with the eyelid and to be completely covered by the eyelid, while the first surface is in contact with the surface of the eye;
   a plurality of stimulation electrodes closer to the first surface than the second surface, wherein the plurality of stimulation electrodes is configured to stimulate the surface of the eye;
   an energy storage element coupled to the plurality of stimulation electrodes; and
   a coil coupled to the energy storage element, wherein the coil is configured to wirelessly receive power for supplying power to the device.

2. The device of claim 1, further comprising:
   a plurality of heating elements closer to second surface than the first surface, wherein the plurality of heating elements is configured to heat the eyelid.

3. The device of claim 2, wherein heating one or more of the plurality of heating elements is coordinated with activating one or more of the plurality of stimulation electrodes to heat the eyelid while the sclera is stimulated.

4. The device of claim 1, wherein the device further comprises:
   a processor configured to control a supply of power from the energy storage element to apply a stimulation waveform to at least one of the plurality of stimulation electrodes.

5. The device of claim 1, wherein the energy storage element comprises a capacitor.

6. The device of claim 1, wherein the energy storage element is configured to:
   receive power from the coil; and
   supply power to the plurality of stimulation electrodes.

7. The device of claim 1, wherein the coil comprises an antenna.

8. The device of claim 1, wherein the coil is further configured to:
   receive power wirelessly from an external device; and
   provide power to the energy storage element.

9. The device of claim 1, wherein the first surface and the second surface comprise a covering selected from one of a silicone elastomer or a silicone hydrogel.

10. The device of claim 1, wherein the energy storage element comprises a battery.

11. A device configured to be placed beneath an eyelid, positioned between the eyelid and a surface of an eye, and worn by a user, the device comprising:
    a first surface configured to:
       oppose a portion of a sclera of the eye; and
       contact the surface of the eye;
    a second surface configured to remain entirely covered by the eyelid while the first surface contacts the surface of the eye;
    a plurality of stimulation electrodes closer to the first surface than the second surface, wherein the plurality of stimulation electrodes is configured to stimulate the eye;
    an energy storage element coupled to the plurality of stimulation electrodes; and
    an electrical component coupled to the energy storage element, wherein the electrical component is configured to wirelessly receive power for supplying power to the device.

12. The device of claim 11, further comprising:
    a plurality of heating elements closer to second surface than the first surface, wherein the plurality of heating elements is configured to heat the eyelid.

13. The device of claim 12, further configured to coordinate heating one or more of the plurality of heating elements with activating one or more of the plurality of stimulation electrodes to heat the eyelid while the sclera is stimulated.

14. The device of claim 11, wherein the device further comprises:
    a processor configured to control a supply of power from the energy storage element to apply a stimulation waveform to at least one of the plurality of stimulation electrodes.

15. The device of claim 11, wherein the energy storage element comprises a capacitor.

16. The device of claim 11, wherein the energy storage element is configured to:
    receive power from the electrical component; and
    supply power to the plurality of stimulation electrodes.

17. The device of claim 11, wherein the electrical component comprises an antenna.

18. The device of claim 11, wherein the electrical component is further configured to:
    receive power wirelessly from an external device; and
    provide power to the energy storage element.

19. The device of claim 11, wherein the first surface and the second surface comprise a covering selected from one of a silicone elastomer or a silicone hydrogel.

20. The device of claim 11, wherein the energy storage element comprises a battery.

* * * * *